US006090587A

United States Patent [19]
Rhodes et al.

[11] Patent Number: 6,090,587
[45] Date of Patent: Jul. 18, 2000

[54] PROKARYOTIC EXPRESSION OF MHC PROTEINS

[75] Inventors: Eric T. Rhodes, Vallejo; Bishwajit Nag, Fremont, both of Calif.

[73] Assignee: Corixa Corporation, Seattle, Wash.

[21] Appl. No.: 08/470,535

[22] Filed: Jun. 6, 1995

Related U.S. Application Data

[60] Division of application No. 08/329,010, Oct. 25, 1994, which is a continuation-in-part of application No. 08/143,575, Oct. 25, 1993, abandoned.

[51] Int. Cl.[7] .............................. C12P 21/06; C12N 1/21; C12N 15/12; C12N 15/63
[52] U.S. Cl. .................... 435/69.3; 435/69.1; 435/252.3; 435/252.33; 435/320.1; 530/300; 530/350; 530/402
[58] Field of Search .................................. 435/69.3, 252, 435/252.33, 69.1, 320.1; 530/300, 350, 402

[56] References Cited

U.S. PATENT DOCUMENTS

| 5,130,297 | 7/1992 | Sharma . |
| 5,194,425 | 3/1993 | Sharma . |
| 5,314,813 | 5/1994 | Peterson .............................. 435/172.3 |

OTHER PUBLICATIONS

Lechler et al J Immunology 144 (1) 329–333, Jan. 1, 1990.
Levy et al. J Immunology 134 (2) 667–683, Feb. 1, 1985.
Sant et al. PNAS USA 84 8065–8069, Nov. 1, 1987.
Squires et al. 263 (31) 16297–16302, Nov. 5, 1988.
Davis, Alan R., et al. (1983) "Immune response to human influenza virus hemagglutinin expressed in *Escherichia coli*", *Gene* 21:273–284.
Fraser, Thomas H., et al. (1978) "Chicken ovalbumin is synthesized and secreted by *Escherichia coli*", *Proc. Natl. Acad. Sci. USA*, 75(12):5936–5940.
Goss, John A., et al. (1993) "Specific prolongation of allograft survival by a T–cell receptor–derived peptide", *Proc. Natl. Acad. Sci. USA*, 90:9872–9876.
Talmadge, Karen, et al. (1980) "Bacteria mature preproinsulin to proinsulin", *Proc. Natl. Acad. Sci USA*, 77(7):3988–3992.
Goeddel, David V., et al. (1979) "Expression in *Escherichia coli* of chemically synthesized genes for human insulin", 76(1):106–110.
Margulies, David H., et al. (1987) "Engineering Soluble Major Histocompatibility Molecules: Why and How", *Immunol. Res.* 6:101–116.
Schein, Catherine H. (1989) "Production of Soluble Recombinant Proteins in Bacteria" (Review), *Bio/Tehcnology*, 7:1141–1149.
Gorga, Joan C. (1992) "Structural Analysis of Class II Major Histocompatibility Complex Proteins", *Critical Reviews in Immunology*, 11(5):305–335.
Goeddel, David, V., et al. (1908) "Human leukocyte interferon produced by *E. coli* is biologically active", *Nature*, 287:411–416.
Stern, Lawrence J., et al. (1992) "The Human Class II MHC Protein HLA–DR1 Assembles as Empty αβ Heterodimers in the Absence of antigenic Peptide", *Cell*, 68:465–477.
Peterson, Mary, et al. (1990) "Invariant chain influences the immunological recognition of MHC class II molecules", *Nature*, 345:172–174.
Luckow, Verne A., et al. (1989) "High Level Expression of Non–fused Foreign Genes with *Autographa californica* Nuclear Polyhedrosis Virus Expression Vectors", *Virology*, 170:31–39.
German, Ronald N., et al. (1991) "MHC class II structure, occupancy and surface expression determined by post–endoplasmic reticulum antigen binding", *Nature*, 353:134–139.
Jackson, Michael R., et al. (1992) "Empty and peptide–containing conformers of class I major histocompatibilty complex molecules expressed in *Drosophila melanogaster* cells", *Proc. Natl. Acad. Sci. USA*, 89:12117–12121.

*Primary Examiner*—Lynette F. Smith
*Assistant Examiner*—Mary K Zeman
*Attorney, Agent, or Firm*—Townsend and Townsend and Crew

[57] ABSTRACT

The present invention is directed to unglycosylated, prokaryoticauly-expressed MHC polypeptides, methods of producing these polypeptides, and complexes consisting essentially of an isolated MHC component and an antigenic peptide associated with the antigen binding site of the MHC component. These complexes are useful in treating deleterious immune responses, such as autoimmunity.

8 Claims, 6 Drawing Sheets

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

TATGGCTAGC ATGACTGGTG GACAGCAAAT GGGTGCCCTA GGCTTCGAAT CTAA                54

(2) INFORMATION FOR SEQ ID NO:2:

```
    (i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

ACCGATCGTA CTGACCACCT GTCGTTTACC CAGCCCTAGG CTTCGAATCT AA          52

(2) INFORMATION FOR SEQ ID NO:3:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

AATTCCTACG TA                                                     12

(2) INFORMATION FOR SEQ ID NO:4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GGATGCATCT AG                                                     12

(2) INFORMATION FOR SEQ ID NO:5:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CGGGATCCGA TCGTGGAGGA TGATTAAATG ATCAAAGAAG AACATGTGAT CATC        54

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GTCGAATTCT TACAGAGGCC CCCTGCGTT                                   29

(2) INFORMATION FOR SEQ ID NO:7:

(i) SEQUENCE CHARACTERISTICS:
        (A) LENGTH: 31 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO:7:

ATCGAATTCA GTTCTCTGTA GTCTCTGGGA G                              31

(2) INFORMATION FOR SEQ ID NO:8:

(i) SEQUENCE CHARACTERISTICS:
         (A) LENGTH: 49 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:8:

CGGGATCCGA TCGTGGAGGA TGATTAAATG GGGGACACCC GACCACGTT           49

(2) INFORMATION FOR SEQ ID NO:9:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:9:

GTCGAATTCT CAGCTCACGA GTCCTGTTGG                                30

(2) INFORMATION FOR SEQ ID NO:10:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:10:

ATCGAATTCA CTTGCTCTGT GCAGATTCAG A                              31

(2) INFORMATION FOR SEQ ID NO:11:

(i) SEQUENCE CHARACTERISTICS:
         (A) LENGTH: 690 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: CDS
         (B) LOCATION: 1..690

(ix) FEATURE:
         (A) NAME/KEY: misc_feature
         (B) LOCATION: 577..690
         (D) OTHER INFORMATION: /note= "Encodes the transmembrane
              region within HLA DR2-Dw2 Alpha Chain."

(xi) SEQUENCE DESCRIPTION: SEQ ID NO:11:

ATC AAA GAA GAA CAT GTG ATC ATC CAG GCC GAG TTC TAT CTG AAT CCT      48
Ile Lys Glu Glu His Val Ile Ile Gln Ala Glu Phe Tyr Leu Asn Pro
 1               5                  10                  15

```
GAC CAA TCA GGC GAG TTT ATG TTT GAC TTT GAT GGT GAT GAG ATT TTC        96
Asp Gln Ser Gly Glu Phe Met Phe Asp Phe Asp Gly Asp Glu Ile Phe
             20                  25                  30

CAT GTG GAT ATG GCA AAG AAG GAG ACG GTC TGG CGG CTT GAA GAA TTT       144
His Val Asp Met Ala Lys Lys Glu Thr Val Trp Arg Leu Glu Glu Phe
         35                  40                  45

GGA CGA TTT GCC AGC TTT GAG GCT CAA GGT GCA TTG GCC AAC ATA GCT       192
Gly Arg Phe Ala Ser Phe Glu Ala Gln Gly Ala Leu Ala Asn Ile Ala
 50                  55                  60

GTG GAC AAA GCC AAC CTG GAA ATC ATG ACA AAG CGC TCC AAC TAT ACT       240
Val Asp Lys Ala Asn Leu Glu Ile Met Thr Lys Arg Ser Asn Tyr Thr
 65                  70                  75                  80

CCG ATC ACC AAT GTA CCT CCA GAG GTA ACT GTG CTC ACG AAC AGC CCT       288
Pro Ile Thr Asn Val Pro Pro Glu Val Thr Val Leu Thr Asn Ser Pro
                 85                  90                  95

GTG GAA CTG AGA GAG CCC AAC GTC CTC ATC TGT TTC ATC GAC AAG TTC       336
Val Glu Leu Arg Glu Pro Asn Val Leu Ile Cys Phe Ile Asp Lys Phe
            100                 105                 110

ACC CCA CCA GTG GTC AAT GTC ACG TGG CTT CGA AAT GGA AAA CCT GTC       384
Thr Pro Pro Val Val Asn Val Thr Trp Leu Arg Asn Gly Lys Pro Val
        115                 120                 125

ACC ACA GGA GTG TCA GAG ACA GTC TTC CTG CCC AGG GAA GAC CAC CTT       432
Thr Thr Gly Val Ser Glu Thr Val Phe Leu Pro Arg Glu Asp His Leu
    130                 135                 140

TTC CGC AAG TTC CAC TAT CTC CCC TTC CTG CCC TCA ACT GAG GAC GTT       480
Phe Arg Lys Phe His Tyr Leu Pro Phe Leu Pro Ser Thr Glu Asp Val
145                 150                 155                 160

TAC GAC TGC AGG GTG GAG CAC TGG GGC TTG GAT GAG CCT CTT CTC AAG       528
Tyr Asp Cys Arg Val Glu His Trp Gly Leu Asp Glu Pro Leu Leu Lys
                165                 170                 175

CAC TGG GAG TTT GAT GCT CCA AGC CCT CTC CCA GAG ACT ACA GAG AAC       576
His Trp Glu Phe Asp Ala Pro Ser Pro Leu Pro Glu Thr Thr Glu Asn
            180                 185                 190

GTG GTG TGT GCC CTG GGC CTG ACT GTG GGT CTG GTG GGC ATC ATT ATT       624
Val Val Cys Ala Leu Gly Leu Thr Val Gly Leu Val Gly Ile Ile Ile
        195                 200                 205

GGG ACC ATC TTC ATC ATC AAG GGA GTG CGC AAA AGC AAT GCA GCA GAA       672
Gly Thr Ile Phe Ile Ile Lys Gly Val Arg Lys Ser Asn Ala Ala Glu
    210                 215                 220

CGC AGG GGG CCT CTG TAA                                               690
Arg Arg Gly Pro Leu
225                 230
```

(2) INFORMATION FOR SEQ ID NO:12:

(i) SEQUENCE CHARACTERISTICS:
        (A) LENGTH: 229 amino acids
        (B) TYPE: amino acid
        (D) TOPOLOGY: linear (ii) MOLECULE TYPE: protein (xi) SEQUENCE DESCRIPTION: SEQ ID NO:12:

```
Ile Lys Glu Glu His Val Ile Ile Gln Ala Glu Phe Tyr Leu Asn Pro
 1               5                  10                  15

Asp Gln Ser Gly Glu Phe Met Phe Asp Phe Asp Gly Asp Glu Ile Phe
             20                  25                  30

His Val Asp Met Ala Lys Lys Glu Thr Val Trp Arg Leu Glu Glu Phe
         35                  40                  45

Gly Arg Phe Ala Ser Phe Glu Ala Gln Gly Ala Leu Ala Asn Ile Ala
```

```
        50                  55                  60
Val Asp Lys Ala Asn Leu Glu Ile Met Thr Lys Arg Ser Asn Tyr Thr
 65                  70                  75                  80

Pro Ile Thr Asn Val Pro Pro Glu Val Thr Val Leu Thr Asn Ser Pro
                     85                  90                  95

Val Glu Leu Arg Glu Pro Asn Val Leu Ile Cys Phe Ile Asp Lys Phe
                100                 105                 110

Thr Pro Pro Val Val Asn Val Thr Trp Leu Arg Asn Gly Lys Pro Val
                115                 120                 125

Thr Thr Gly Val Ser Glu Thr Val Phe Leu Pro Arg Glu Asp His Leu
                130                 135                 140

Phe Arg Lys Phe His Tyr Leu Pro Phe Leu Pro Ser Thr Glu Asp Val
145                 150                 155                 160

Tyr Asp Cys Arg Val Glu His Trp Gly Leu Asp Glu Pro Leu Leu Lys
                165                 170                 175

His Trp Glu Phe Asp Ala Pro Ser Pro Leu Pro Glu Thr Thr Glu Asn
                180                 185                 190

Val Val Cys Ala Leu Gly Leu Thr Val Gly Leu Val Gly Ile Ile Ile
                195                 200                 205

Gly Thr Ile Phe Ile Ile Lys Gly Val Arg Lys Ser Asn Ala Ala Glu
    210                 215                 220

Arg Arg Gly Pro Leu
225

(2) INFORMATION FOR SEQ ID NO:13:

(i) SEQUENCE CHARACTERISTICS:
        (A) LENGTH: 714 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: CDS
         (B) LOCATION: 1..714

(ix) FEATURE:
         (A) NAME/KEY: misc_feature
         (B) LOCATION: 595..714
         (D) OTHER INFORMATION: /note= "Encodes the trans-membrane
             region within HLA DR2-Dw2 Beta Chain."

(xi) SEQUENCE DESCRIPTION: SEQ ID NO:13:

GGG GAC ACC CGA CCA CGT TTC TTG CAG CAG GAT AAG TAT GAG TGT CAT          48
Gly Asp Thr Arg Pro Arg Phe Leu Gln Gln Asp Lys Tyr Glu Cys His
 1               5                  10                  15

TTC TTC AAC GGG ACG GAG CGG GTG CGG TTC CTG CAC AGA GAC ATC TAT         96
Phe Phe Asn Gly Thr Glu Arg Val Arg Phe Leu His Arg Asp Ile Tyr
                20                  25                  30

AAC CAA GAG GAG GAC TTG CGC TTC GAC AGC GAC GTG GGG GAG TAC CGG        144
Asn Gln Glu Glu Asp Leu Arg Phe Asp Ser Asp Val Gly Glu Tyr Arg
            35                  40                  45

GCG GTG ACG GAG CTG GGG CGG CCT GAC GCT GAG TAC TGG AAC AGC CAG        192
Ala Val Thr Glu Leu Gly Arg Pro Asp Ala Glu Tyr Trp Asn Ser Gln
        50                  55                  60

AAG GAC TTC CTG GAA GAC AGG CGC GCC GCG GTG GAC ACC TAC TGC AGA        240
Lys Asp Phe Leu Glu Asp Arg Arg Ala Ala Val Asp Thr Tyr Cys Arg
 65                 70                  75                  80

CAC AAC TAC GGG GTT GGT GAG AGC TTC ACA GTG CAG CGG CGA GTT GAG        288
```

```
His Asn Tyr Gly Val Gly Glu Ser Phe Thr Val Gln Arg Arg Val Glu
                85                  90                  95

CCT AAG GTG ACT GTG TAT CCT GCA AGG ACC CAG ACC CTG CAG CAC CAC       336
Pro Lys Val Thr Val Tyr Pro Ala Arg Thr Gln Thr Leu Gln His His
            100                 105                 110

AAC CTC CTG GTC TGC TCT GTG AGT GGT TTC TAT CCA GCC AGC ATT GAA       384
Asn Leu Leu Val Cys Ser Val Ser Gly Phe Tyr Pro Ala Ser Ile Glu
        115                 120                 125

GTC AGG TGG TTC CGG AAC AGC CAG GAA GAG AAG GCT GGG GTG GTG TCC       432
Val Arg Trp Phe Arg Asn Ser Gln Glu Glu Lys Ala Gly Val Val Ser
    130                 135                 140

ACA GGC CTG ATT CAG AAT GGA GAC TGG ACC TTC CAG ACC CTG GTG ATG       480
Thr Gly Leu Ile Gln Asn Gly Asp Trp Thr Phe Gln Thr Leu Val Met
145                 150                 155                 160

CTG GAA ACA GTT CCT CGA AGT GGA GAG GTT TAC ACC TGC CAA GTG GAG       528
Leu Glu Thr Val Pro Arg Ser Gly Glu Val Tyr Thr Cys Gln Val Glu
                165                 170                 175

CAC CCA AGC GTG ACG AGC CCT CTC ACA GTG GAA TGG AGA GCA CAG TCT       576
His Pro Ser Val Thr Ser Pro Leu Thr Val Glu Trp Arg Ala Gln Ser
            180                 185                 190

GAA TCT GCA CAG AGC AAG ATG CTG AGT GGA GTC GGG GGC TTT GTG CTG       624
Glu Ser Ala Gln Ser Lys Met Leu Ser Gly Val Gly Gly Phe Val Leu
        195                 200                 205

GGC CTG CTC TTC CTT GGG GCC GGG CTA TTC ATC TAC TTC AAG AAT CAG       672
Gly Leu Leu Phe Leu Gly Ala Gly Leu Phe Ile Tyr Phe Lys Asn Gln
    210                 215                 220

AAA GGG CAC TCT GGA CTT CAC CCA ACA GGA CTC GTG AGC TGA               714
Lys Gly His Ser Gly Leu His Pro Thr Gly Leu Val Ser
225                 230                 235

(2) INFORMATION FOR SEQ ID NO:14:

(i) SEQUENCE CHARACTERISTICS:
        (A) LENGTH: 237 amino acids
        (B) TYPE: amino acid
        (D) TOPOLOGY: linear (ii) MOLECULE TYPE: protein (xi) SEQUENCE DESCRIPTION: SEQ ID NO:14:

Gly Asp Thr Arg Pro Arg Phe Leu Gln Gln Asp Lys Tyr Glu Cys His
1               5                   10                  15

Phe Phe Asn Gly Thr Glu Arg Val Arg Phe Leu His Arg Asp Ile Tyr
            20                  25                  30

Asn Gln Glu Glu Asp Leu Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Phe Leu Glu Asp Arg Arg Ala Ala Val Asp Thr Tyr Cys Arg
65                  70                  75                  80

His Asn Tyr Gly Val Gly Glu Ser Phe Thr Val Gln Arg Arg Val Glu
                85                  90                  95

Pro Lys Val Thr Val Tyr Pro Ala Arg Thr Gln Thr Leu Gln His His
            100                 105                 110

Asn Leu Leu Val Cys Ser Val Ser Gly Phe Tyr Pro Ala Ser Ile Glu
        115                 120                 125

Val Arg Trp Phe Arg Asn Ser Gln Glu Glu Lys Ala Gly Val Val Ser
    130                 135                 140

Thr Gly Leu Ile Gln Asn Gly Asp Trp Thr Phe Gln Thr Leu Val Met
```

```
145                 150                 155                 160

Leu Glu Thr Val Pro Arg Ser Gly Glu Val Tyr Thr Cys Gln Val Glu
            165                 170                 175

His Pro Ser Val Thr Ser Pro Leu Thr Val Glu Trp Arg Ala Gln Ser
            180                 185                 190

Glu Ser Ala Gln Ser Lys Met Leu Ser Gly Val Gly Phe Val Leu
        195                 200                 205

Gly Leu Leu Phe Leu Gly Ala Gly Leu Phe Ile Tyr Phe Lys Asn Gln
        210                 215                 220

Lys Gly His Ser Gly Leu His Pro Thr Gly Leu Val Ser
225                 230                 235
```

(2) INFORMATION FOR SEQ ID NO:15:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
CGGAATTCCG                                                              10
```

(2) INFORMATION FOR SEQ ID NO:16:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

```
TCAGGATCCG ATCGTGGAGG ATGATTAAAT GCAAATTTTT GTCAAGACTT TGACTGGT        58
```

(2) INFORMATION FOR SEQ ID NO:17:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

```
TGAATTCCCG CGGAGTCTCA AGACTAAGTG CAAAGTGGA                              39
```

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

```
ATCCGCGGGG GCATCAAAGA AGAACATGTG ATCATC                                 36
```

(2) INFORMATION FOR SEQ ID NO:19:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:19:

GTCGAATTCT TACAGAGGCC CCCTGCGTT                                29

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

GTCGAATTCT CAGTTCTCTG TAGTCTCTGG GAG                            33

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

ATCGAATTCT TAAGCATCAA ACTCCCAGTG CTT                            33

(2) INFORMATION FOR SEQ ID NO:22:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

CGGGATCCGA TCGTGGAGGA TGATTAAATG ATCAAAGAAG AACATGTGAT CAT       53

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

ATCGAATTCT TAAGCATCAA ACTCCCAGTG CTT                            33

(2) INFORMATION FOR SEQ ID NO:24:

(i) SEQUENCE CHARACTERISTICS:
        (A) LENGTH: 26 base pairs
        (B) TYPE: nucleic acid -continued

```
            (C) STRANDEDNESS: single
            (D) TOPOLOGY: linear (ii) MOLECULE TYPE: DNA (xi) SEQUENCE DESCRIPTION: SEQ ID NO:24:

ATCTCGAGTT TGACAGCTTA TCATCG                                          26

(2) INFORMATION FOR SEQ ID NO:25:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:25:

ATCTCGAGTC AGGTCGAGGT GGC                                             23
```

PROKARYOTIC EXPRESSION OF MHC PROTEINS

This application is a division of U.S. application Ser. No. 08/329,010, filed Oct. 25, 1994 which is a continuation-in-part of U.S. application Ser. No. 08/143,575, filed Oct. 25, 1993, now abandoned, all of which are hereby incorporated in their entirety by reference.

BACKGROUND OF THE INVENTION

The invention relates to methods of producing compositions for the modulation of T cell function in the treatment of for example, autoimmune diseases, allergic responses, transplant rejection, and other immunological disorders. In particular, it concerns production of major histocompatibility complex (MHC) class I and class II proteins in prokaryotes that have been transformed with nucleotide sequences that code for the proteins. The MHC proteins are useful for making complexes that target T cells. The complexes comprise the MHC proteins and peptides representing fragments of antigens associated with the particular diseases. These complexes can be further conjugated to radioisotopes or other labels for diagnostic purposes, or to toxins or other substances which render the complexes therapeutically useful.

A number of pathological responses involving unwanted T cell activation are known. For instance, a number of allergic diseases have been associated with particular MHC alleles or are suspected of having an autoimmune component.

Other deleterious T cell-mediated responses include the destruction of foreign cells that are purposely introduced into the body as grafts or transplants from allogeneic hosts. This process, known as "allograft rejection," involves the interaction of host T cells with foreign MHC molecules. Quite often, a broad range of MHC alleles are involved in the response of the host to an allograft.

Autoimmune disease is a particularly important class of deleterious immune response. In autoimmune diseases, self-tolerance is lost and the immune system attacks "self" tissue as if it were a foreign target. More than 30 autoimmune diseases are presently known; these include many which have received much public attention, including myasthenia gravis (MG) and multiple sclerosis (MS).

The involvement of the MHC Class II proteins in autoimmune disease has been shown in animal models. Administration of antibodies to either MHC Class II proteins themselves or antibodies to agents that induce expression of the MHC Class II genes interferes with development of the autoimmune condition in these model systems. The role of helper T cells has also been demonstrated in these models by counteracting the autoimmune system using anti-CD4 monoclonal antibodies: CD4 is the characteristic helper T cell receptor (Shizuru, J. A. et al., *Science* (1988) 240: 659–662).

Recent experiments have shown that, under certain circumstances, anergy or nonresponsiveness can be induced in autoreactive lymphocytes (see, Schwartz, *Cell* (1989) 1073–1081). In vitro experiments suggest that antigen presentation by MHC Class II molecules in the absence of a co-stimulatory signal induces a state of proliferative non-responsiveness in syngeneic T cells (Quill et al., *J. Immunol.* (1987) 138: 3704–3712). As described by Sharma et al. (*Proc. Natl. Acad. Sci. USA* (1991) 88: 11465–11469) anergy can be induced in vivo and autoimmune disease can be effectively treated in this manner.

MHC polypeptides thus have several pharmaceutical uses. However, to realize the potential of these types of treatments, a source of abundant MHC polypeptides is needed. MHC polypeptides have been expressed in mammalian cells. For example, a soluble form of the mouse I-E$^k$ protein has been expressed in CHO cells (Wettsttein et. al., *J. Exp. Med.* 174: 219–228 (1991)). The expression levels from mammalian systems, however, are not sufficient for economical production of MHC polypeptides on a commercial scale. Moreover, mammalian cells load the MHC peptide binding pocket with endogenous peptides, necessitating peptide removal from the MHC. Thus, the prior art lacks methods for producing large quantities of therapeutically active MHC polypeptides at low cost. The present invention addresses these and other needs.

SUMMARY OF THE INVENTION

The present invention provides compositions comprising recombinant MHC polypeptides having altered glycosylation, in which the recombinant MHC polypeptide binds an antigenic peptide. The transmembrane domain is lacking from some of the recombinant constructs which are disclosed. The MHC polypeptide compositions are expressed in a prokaryotic host cell such as *E. coli* utilizing an expression vector containing a nucleotide sequence encoding the MHC polypeptide. MHC class II recombinant polypeptides are disclosed, including the α- and β-chains. Multiple recombinant MHC polypeptides are optionally associated to form active MHC compositions.

The present invention includes a method of producing an MHC polypeptide comprising the steps of (a) growing in a culture prokaryotic cells containing an expression vector comprising a nucleotide sequence encoding the MHC polypeptide under such conditions that the polypeptide is expressed: and (b) extracting and isolating the MHC polypeptide. The method provides for the expression of two MHC polypeptides in a single prokaryotic cell, wherein the polypeptides form a heterodimer. The compositions produced by the method are also the subject of the invention.

The invention further provides for a prokaryotic expression vector comprising a nucleotide sequence coding for an MHC polypeptide operably linked to a prokaryotic promoter sequence. A signal sequence operably liked to the MHC polypeptide sequence is optionally included in the vector. The nucleotide sequence for the MHC polypeptide can encode a truncated MHC polypeptide, or an MHC polypeptide lacking a transmembrane domain, in addition to full-length MHC polypeptides and other constructs which are derived from the full-length MHC polypeptide. The vector can be used to transform a prokaryotic cell such as *E. coli*.

The invention additionally provides for a substantially pure MHC-peptide complex consisting essentially of an antigenic peptide and an isolated recombinant MHC component having altered glycosylation and an antigen binding site, wherein the antigenic peptide is associated with the antigen binding site. The peptide is typically between about 8 and about 30 amino acids, but can be shorter or longer. The peptide can be noncovalently associated with the antigen binding site. The present invention includes peptides which are autoantigenic and thereby associated with an autoimmune disease. An epitope on the peptide can be recognized, for example, by an autoreactive T cell associated with multiple sclerosis, rheumatoid arthritis, or myasthenia gravis. Suitable peptide include those comprising residues 138–167 of human AChR α subunit, residues 84–102 of human MBP, and residues 148–162 of human MBP.

Also provided are pharmaceutical compositions comprising a pharmaceutically acceptable carrier and the recombinant MHC-peptide complex. An example of the pharmaceutical composition includes a composition in which the MHC-peptide complex is embedded in a liposome.

Definitions

A "nucleotide sequence encoding an MHC polypeptide" is a subsequence or full length polynucleotide sequence which, when present in a cell, expresses an MHC polypeptide. In the expression of recombinant constructs one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the above term. In addition, reference to polynucleotides of the invention specifically includes those full length sequences substantially identical (determined as described below) with an MHC gene sequence and that encode proteins that retain the function of the MHC polypeptides. Thus, in the case of the sequences encoding MHC single subunits disclosed here, the term includes variant polynucleotide sequences which have substantial identity with the sequences disclosed here and which encode proteins capable of binding antigenic peptides and binding a T cell receptor. The polypeptides of the present invention can consist of a full length MHC subunits, or a fragment thereof.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85: 2444 (1988), and by computerized implementations of these algorithms. Typically, the program providing the highest percentage identity is used.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 70% sequence identity, preferably at least 80%, more preferably at least 90% and most preferably at least 95%, compared to a reference sequence using the programs described above using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 70%, preferably at least 80%, more preferably at least 90%, and most preferably at least 95%.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C.

Another indication that protein sequences are substantially identical is if one protein is immunologically reactive with antibodies raised against the other protein. Thus, the proteins of the invention include proteins immunologically reactive with antibodies raised against MHC polypeptides.

As used herein, the terms "isolated", "substantially pure" and "substantially homogenous" are used to describe a protein that has been separated from components which naturally accompany it. Typically, a monomeric protein is substantially pure when at least about 60 to 75% of a sample exhibits a single polypeptide backbone. Minor variants or chemical modifications typically share the same polypeptide sequence. A substantially purified protein will typically comprise over about 85 to 90% of a protein sample, more usually about 95%, and preferably will be over about 99% pure, either by mass or by molecular numbers. Protein purity or homogeneity may be indicated by a number of means well known in the art, such as polyacrylamide gel electrophoresis of a protein sample, followed by visualizing a single polypeptide band on a polyacrylamide gel upon staining. For certain purposes high resolution will be needed and HPLC or a similar means utilized for purification.

The term "MHC polypeptide" as used herein refers to a single chain MHC protein (e.g., the α or β chain of Class II molecules or the heavy chain of Class I molecules) which may constitute all or part of the effective portion of the MHC complex (i.e., a peptide comprising an antigen binding site or sites and sequences necessary for recognition by the appropriate T cell receptor) which is in other than its native state, for example, not associated with the cell membrane of a cell that normally expresses MHC.

The term "altered glycosylation" refers to glycosylation of the MHC polypeptide in which the polypeptide is unglycosylated, or has a glycosylation pattern which differs from that found on the native polypeptide. Altered glycosylation in this application refers to glycosylation achieved through in vivo processes, but does not refer to in vitro processes such as treatment of the MHC polypeptide with an enzyme or chemical to produce a deglycosylated molecule.

An "unglycosylated recombinant MHC polypeptide" is an MHC class I or class II polypeptide that lacks substantially all naturally occurring glycosylation. Typically, the polypeptides of the invention will have less than about ten percent of the glycosylation observed when MHC polypeptides are produced in human cells. More preferably, the polypeptides will have less than about five percent, and most preferably less than about one percent of the carbo-hydrates attached to MHC polypeptides produced in human cells.

The unglycosylated recombinant MHC polypeptides of the invention are typically produced by a prokaryotic host cell that has been transformed with a nucleotide sequence that encodes the MHC polypeptide. Recombinant DNA techniques are generally used to link the MHC-encoding nucleotide sequence to signals that control gene expression. As a consequence of being produced in prokaryotic host cells, the MHC polypeptides lack the carbohydrate moieties that are normally found on MHC polypeptides from eukaryotic cells.

DESCRIPTION OF THE PREFERRED EMBODIMENT

Figure 1:
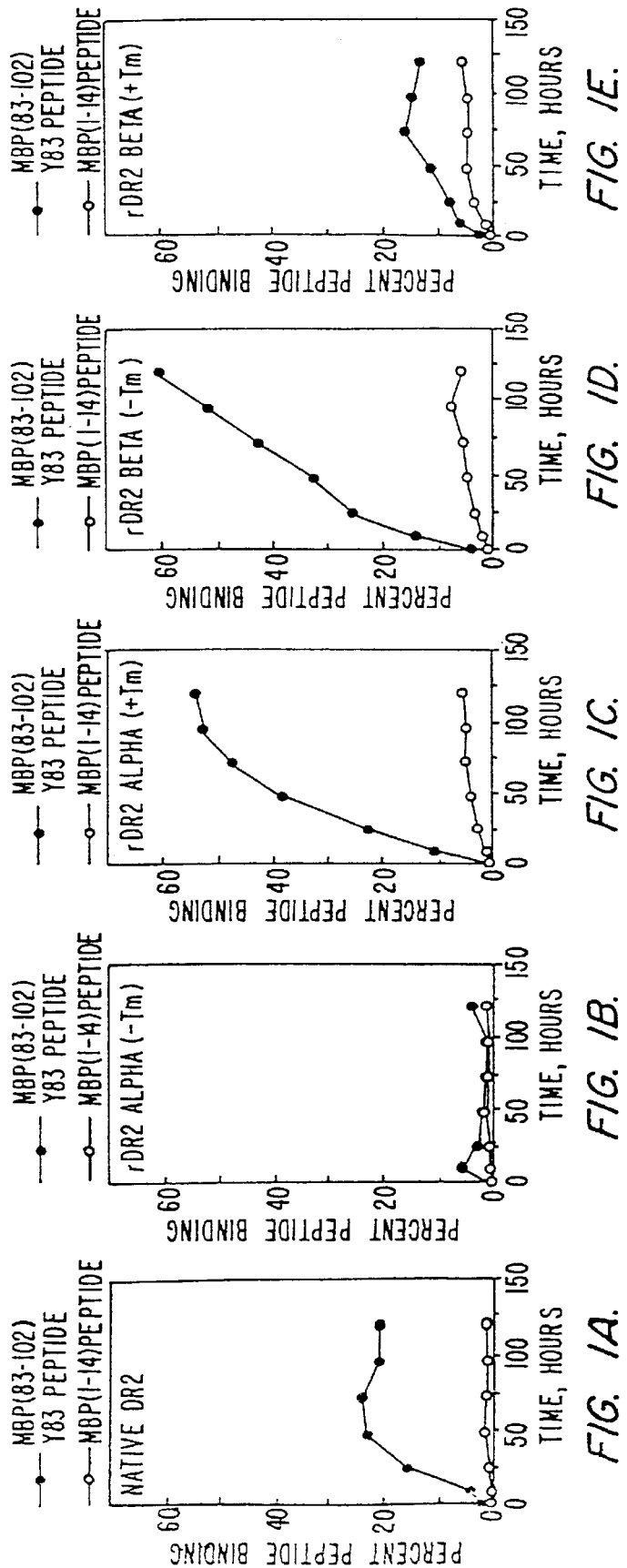
FIG. 1 shows kinetics of peptide binding to recombinant DR2 chains expressed in E. coli.

The present invention provides recombinant MHC polypeptides that can be used to form complexes useful for modulating T cell function, and methods for producing the MHC polypeptides. The complexes, which consist of the MHC polypeptides complexed with antigenic peptides, can be used to inhibit a deleterious T cell-mediated immune response, such as allergic responses, allograft rejection, and autoimmune diseases. In addition, the complexes can be used to promote immune responses and can be used as vaccines.

The present invention also provides methods for producing MHC proteins on a commercially viable scale. A further advantage provided by the present invention is that it provides a readily adaptable means of producing modified MHC polypeptides that are useful for a variety of desired uses. For example, when using the complexes for promoting immune responses or vaccines, it is desirable to modify the MHC polypeptides to allow attachment to a competent antigen presenting cell bearing ligands involved in the costimulatory signal responsible for T cell activation. Alternatively, the MHC complex can be linked to isolated costimulatory ligands such that T cell proliferation is induced. Thus, T cells will respond to the antigenic peptide presented by the complexes and an immune response will be initiated.

The unglycosylated MHC polypeptides of the invention are produced in prokaryotic cells, such as E. coli. The prokaryoticaily-produced MHC polypeptides of the invention bind antigenic peptide with an efficiency similar to that of glycosylated, native MHC polypeptides.

According to the invention, nucleotide sequences that code for the desired MHC polypeptides are isolated and transformed into suitable prokaryotic host cells, which are grown in culture under conditions that result in expression of the MHC polypeptides. The MHC polypeptides are then isolated from the cells or the culture supernatant and associated with the appropriate antigenic peptide to form a complex of the invention. Pharmaceutical compositions are prepared and administered according to standard techniques. For a general description of this approach, see U.S. Pat. Nos. 5,130,297 and 5,194,425.

MHC Polypeptides

The proteins encoded by the MHC have been extensively studied in both the human and murine systems. In general, they have been classified as Class I proteins, found on the surfaces of all cells and primarily recognized by cytotoxic T cells; and Class II proteins which are found on the surfaces of several cells, including accessory cells such as macrophages, and are involved in presentation of antigens to helper T cells. Some of the histocompatibility proteins have been isolated and characterized. For a general review of MHC protein structure and function, see *Fundamental Immunology*, 2d Ed., W. E. Paul, ed., Ravens Press N.Y. 1989.

Several types of MHC complexes have been studied. The MHC complexes encoded by the murine I-A and I-E (class II) subregions have been shown to consist of two noncovalently associated peptide chains: an alpha chain of 32–38 kd and a beta chain of 26–29 kd. A third, invariant, 31 kd peptide is noncovalently associated with these two peptides in the cell and generally dissociates to allow for loading of the antigenic peptide. Surface expression of the invariant chain inhibits the ability of the MHC class II chains to bind and present peptide. The alpha and beta chains of seven allelic variants of the I-A region have been cloned and sequenced (Estees et al., "T cell Clones" in *Regulation of Immune Gene Expression*, Feldman et al., eds. (Humana Press 1985), pp. 3–19. Methods for purifying the murine I-A (Class II) histocompatibility proteins have been disclosed by Turkewitz. A. P., et al., *Molecular Immunology* (1983) 20: 1139–1147. These methods, which are also suitable for Class I molecules, involve preparation of a soluble membrane extract from cells containing the desired MHC molecule using nonionic detergents, such as NP-40, Tween 80 and the like. The MHC molecules are then purified by affinity chromatography, using a column containing antibodies raised against the desired MHC molecule. Use of 0.02% Tween-80 in the elution buffer is helpful to eliminate aggregation of the purified molecules.

The human Class I proteins have also been studied. The MHC of humans (HLA) on chromosome 6 has three loci, HLA-A, HLA-B, and HLA-C, the first two of which have a large number of alleles encoding alloantigens. These are found to consist of a 44 kd subunit and a 12 kd $beta_2$-microglobulin subunit which is common to all antigenic specificities. Isolation of these detergent-soluble HLA antigens was described by Springer, T. A., et al., *Proc. Natl. Acad. Sci. USA* (1976) 73: 2481–2485; Clementson, K. J., et al., in "Membrane Proteins" Azzi, A., ed; Bjorkman, P., Ph.D. Thesis Harvard (1984).

Further work has resulted in a detailed picture of the 3-D structure of HLA-A2, a Class I human antigen. (Bjorkman, P. J., et al., *Nature* (1987) 329: 506–512, 512–518. In this picture, the $\beta_2$-microglobulin protein and alpha$_3$ segment of the heavy chain are associated; the alpha$_1$ and alpha$_2$ regions of the heavy chain appear to form antigen-binding sites to which the peptide is bound (*Science* (1987) 238:613–614, Bjorkman, P. J. et al. *Nature* (supra). Soluble HLA-A2 can be purified after papain digestion of plasma membranes from the homozygous human lymphoblastoid cell line J-Y as described by Turner, M. J. et al., *J. Biol. Chem.* (1977) 252: 7555–7567. Papain cleaves the 44 kd chain close to the transmembrane region yielding a molecule comprised of alpha$_1$, alpha$_2$, alpha$_3$, and $\beta_2$ microglobulin.

The three dimensional structure of human Class II MHC antigens has also been determined and is similar to that of of Class I molecules. Antigenic peptides are bound in an open ended antigen binding groove. The binding groove is formed from the N-terminal domain portions of two class II chains which extend from the membrane bilayer. (Brown. et al., *Nature* 364: 33–39 (1993)). Cloning of the Class II genes (as described by Estees. supra) permits manipulation of the Class II MHC binding domains for example, as described below.

Cloning of MHC Genes

The amino acid sequence of each of a number of Class II proteins are known, and the genes or cDNAs have been cloned. Thus, these nucleic acids can be used to express the MHC polypeptides in a prokaryotic host cell according to the invention, as described herein.

If a desired MHC gene or cDNA is not available, cloning methods known to those skilled in the art may be used to isolate the genes. One such method that can be used is to purify the desired MHC polypeptide, obtain a partial amino acid sequence, synthesize a nucleotide probe based on the amino acid sequence, and use the probe to identify clones that harbor the desired gene from a cDNA or genomic library.

MHC polypeptides can be obtained by isolation from lymphocytes and screened for the ability to bind the desired peptide antigen. The lymphocytes are from the species of individual which will be treated with the complexes. For example, they may be isolated from human B cells from an individual suffering from the targeted autoimmune disease. The B cells can first be immortalized by transformation with a replication deficient Epstein-Barr virus, utilizing techniques known in the art.

MHC polypeptides have been isolated from a multiplicity of cells using a variety of techniques including solubilization by treatment with papain, by treatment with 3M KCl, and by treatment with detergent. In a preferred method detergent extraction of Class II protein from lymphocytes followed by affinity purification is used. Detergent can then be removed by selected methods such as dialysis. Purification methods for MHC polypeptides are also discussed in the preceding section.

After isolation of the enzyme, a partial amino acid sequence is determined and degenerate oligonucleotide probes, designed to hybridize to the desired gene, are synthesized. Amino acid sequencing is performed and oligonucleotide probes are synthesized according to standard techniques as described, for instance, in Sambrook et al., (1989) *Molecular Cloning: A Laboratory Manual* (2nd ed.), Vols. 1–3, Cold Spring Harbor Laboratory.

Genomic or cDNA libraries are prepared according to standard techniques as described, for instance, in Sambrook et al., supra. To construct genomic libraries, large segments of genomic DNA are generated by random fragmentation and are ligated with vector DNA to form concatemers that can be packaged into the appropriate vector. Two kinds of vectors are commonly used for this purpose, bacteriophage lambda vectors and cosmids.

To prepare cDNA, mRNA from the organism of interest is first isolated. Eukaryotic mRNA has at its 3' end a string of adenine nucleotide residues known as the poly-A tail. Short chains of oligo d-T nucleotides are then hybridized with the poly-A tails serving as a primer for the enzyme reverse transcriptase. This enzyme uses RNA as a template to synthesize a complementary DNA (cDNA) strand. A second DNA strand is then synthesized using the first cDNA strand as a template. Linkers are added to the double-stranded cDNA for insertion into a plasmid or $\lambda$ phage vector for propagation in *E. coli*.

Identification of clones in either genomic or cDNA libraries harboring the desired nucleic acid segments is performed by either nucleic acid hybridization, or immunological detection of the encoded protein if an expression vector is used. The bacterial colonies are then replica plated on solid support, such as nitrocellulose filters. The cells are lysed and probed with either oligonucleotide probes described above or with antibodies to the desired protein.

Other methods well known to those skilled in the art can also be used to identify desired genes. For example, amplification techniques, such as the polymerase chain reaction (PCR) can be used to amplify the desired nucleotide sequence. U.S. Pat. Nos. 4,683,195 and 4,683,202 describe this method. Sequences amplified by PCR can be purified from agarose gels and cloned into an appropriate vector according to standard techniques.

Prokaryotic Expression of MHC Polypeptides

Prokaryotes that are useful as host cells, according to the present invention, most frequently are represented by various strains of *E. coli*. However, other microbial strains can also be used, such as bacilli, for example *Bacillus subtilis*, various species of Pseudomonas, or other bacterial strains.

According to the invention, the MHC polypeptides are expressed from cloned nucleotide sequences that encode the MHC polypeptides by operably linking the truncated or full-length nucleic acids to signals that direct gene expression in prokaryotes. A nucleic acid is "operably linked" when it is placed into a functional relationship with another nucleic acid sequence. For instance, a promoter or enhancer is operably linked to a coding sequence if it affects the transcription of the sequence. Generally, operably linked means that the nucleic acid sequences being linked are contiguous and, where necessary to join two protein coding regions, contiguous and in reading frame.

The genes encoding the MHC molecules may be inserted into an "expression vector", "cloning vector", or "vector," terms which are used interchangeably herein and usually refer to plasmids or other nucleic acid molecules that are able to replicate in a chosen host cell. Expression vectors may replicate autonomously, or they can replicate by being inserted into the genome of the host cell, by methods well known in the art. Vectors that replicate autonomously will have an origin of replication or autonomous replicating sequence (ARS) that is functional in the chosen host cell(s).

Plasmid vectors that contain replication sites and control sequences derived from a species compatible with the chosen host are used. For example, *E. coli* is typically transformed using derivatives of pBR322, a plasmid derived from an *E. coli* species by Bolivar et al., *Gene* (1977) 2: 95. Often, it is desirable for a vector to be usable in more than one host cell, e.g., in *E. coil* for cloning and construction, and in a Bacillus cell for expression.

The expression vectors typically contain a transcription unit or expression cassette that contains all the elements required for the expression of the DNA encoding the MHC molecule in the host cells. A typical expression cassette contains a promoter operably linked to the DNA sequence encoding a MHC polypeptide and a ribosome binding site. The promoter is preferably positioned about the same distance from the heterologous transcription start site as it is from the transcription start site in its natural setting. As is known in the art, however, some variation in this distance can be accommodated without loss of promoter function. In addition to a promoter sequence, the expression cassette can also contain a transcription termination region downstream of the structural gene to provide for efficient termination. The termination region may be obtained from the same gene as the promoter sequence or may be obtained from a different gene.

Commonly used prokaryotic control sequences, which are defined herein to include promoters for transcription initiation, optionally with an operator, along with ribosome binding site sequences, include such commonly used promoters as the beta-lactamase (penicillins) and lactose (lac) promoter systems (Change et al., Nature (1977) 198: 1056) and the tryptophan (trp) promoter system (Goeddel et al., Nucleic Acids Res. (1980) 8: 4057) and the lambda-derived $P_L$ promoter and N-gene ribosome binding site (Shimatake et al., Nature (1981) 292: 128). Any available promoter system that functions in prokaryotes can be used.

Either constitutive or regulated promoters can be used in the present invention. Regulated promoters can be advantageous because the host cells can be grown to high densities before expression of the MHC polypeptides is induced. High level expression of heterologous proteins slows cell growth in some situations. Regulated promoters especially suitable for use in E. coli include the bacteriophage lambda $P_L$ promoter, the hybrid trp-lac promoter (Amann et al., Gene (1983) 25: 167; de Boer et al., Proc. Natl. Acad. Sci. USA (1983) 80: 21, and the bacteriophage T7 promoter (Studier et al., J. Mol. Biol. (1986); Tabor et al., (1985). These promoters and their use are discussed in Sambrook et al., supra.

For expression of MHC polypeptides in prokaryotic cells other than E. coli, a promoter that functions in the particular prokaryotic species is required. Such promoters can be obtained from genes that have been cloned from the species, or heterologous promoters can be used. For example, the hybrid trp-lac promoter functions in Bacillus in addition to E. coli.

A ribosome binding site (RBS) is also necessary for expression of MHC polypeptides in prokaryotes. An RBS in E. coli, for example, consists of a nucleotide sequence 3–9 nucleotides in length located 3–11 nucleotides upstream of the initiation codon (Shine and Dalgarno, Nature (1975) 254: 34; Steitz, In Biological regulation and development: Gene expression (ed. R. F. Goldberger), vol. 1, p. 349, 1979, Plenum Publishing, N.Y.).

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), J. Biol. Chem. 263: 16297–16302.

The MHC polypeptides can be expressed intracellularly, or can be secreted from the cell. Intracellular expression often results in high yields. However, some of the protein may be in the form of insoluble inclusion bodies. Although intracellularly produced MHC polypeptides of the present invention are active upon being harvested following cell lysis, the amount of soluble, active MHC polypeptide may be increased by performing refolding procedures (see, e.g., Sambrook et al., supra.; Marston er al., Bio/Technology (1984) 2: 800; Schoner et al., Bio/Technology (1985) 3: 151). More than one MHC polypeptide may be expressed in a single prokaryotic cell by placing multiple transcriptional cassettes in a single expression vector, or by utilizing different selectable markers for each of the expression vectors which are employed in the cloning strategy.

A second approach for expressing the MHC polypeptides of the invention is to cause the polypeptides to be secreted from the cell, either into the periplasm or into the extracellular medium. The DNA sequence encoding the MHC polypeptide is linked to a cleavable signal peptide sequence. The signal sequence directs translocation of the MHC polypeptide through the cell membrane. An example of a suitable vector for use in E. coli that contains a promoter-signal sequence unit is pTA1529, which has the E. coli phoA promoter and signal sequence (see, e.g., Sambrook et al., supra.; Oka et al., Proc. Natl. Acad. Sci. USA (1985) 82: 7212; Talmadge et al., Proc. Natl. Acad. Sci. USA (1980) 77: 3988; Takahara et al., J. Biol. Chem. (1985) 260: 2670). Once again, multiple polypeptides can be expressed in a single cell for periplasmic association.

The MHC polypeptides of the invention can also be produced as fusion proteins. This approach often results in high yields, because normal prokaryotic control sequences direct transcription and translation. In E. coli, lacZ fusions are often used to express heterologous proteins. Suitable vectors are readily available, such as the pUR, pEX, and pMR100 series (see, e.g., Sambrook et al., supra.). For certain applications, it may be desirable to cleave the non-MHC amino acids from the fusion protein after purification. This can be accomplished by any of several methods known in the art, including cleavage by cyanogen bromide, a protease, or by Factor $X_a$ (see, e.g., Sambrook et al., supra.; Itakura et al., Science (1977) 198: 1056; Goeddel et al., Proc. Nail. Acad. Sci. USA (1979) 76: 106; Nagai et al., Nature (1984) 309: 810; Sung et al., Proc. Natl. Acad. Sci. USA (1986) 83: 561). Cleavage sites can be engineered into the gene for the fusion protein at the desired point of cleavage.

A preferred system for obtaining recombinant proteins from E. coil which maintains the integrity of their N-termini has been described by Miller et al. Biotechnology 7:698–704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

The vectors containing the nucleic acids that code for the MHC polypeptide are transformed into prokaryotic host cells for expression. "Transformation" refers to the introduction of vectors containing the nucleic acids of interest directly into host cells by well known methods. The particular procedure used to introduce the genetic material into the host cell for expression of the MHC polypeptide is not particularly critical. Any of the well known procedures for introducing foreign nucleotide sequences into host cells may be used. It is only necessary that the particular procedure utilized be capable of successfully introducing at least one gene into the host cell which is capable of expressing the gene.

Transformation methods, which vary depending on the type of host cell, include electroporation; transfection employing calcium chloride, rubidium chloride calcium phosphate, or other substances; microprojectile bombardment; infection (where the vector is an infectious agent); and other methods. See, generally, Sambrook et al., (1989) supra, and *Current Protocols in Molecular Biology*, supra. Reference to cells into which the nucleic acids described above have been introduced is meant to also include the progeny of such cells. Transformed prokaryotic cells that contain expression vectors for expressing MHC polypeptides are also included in the invention.

After standard transfection or transformation methods are used to produce prokaryotc cell lines that express large quantities of the MHC polypeptide, the polypeptide is then purified using standard techniques. See, e.g., Colley et al. (1989) *J. Biol. Chem.* 64: 17619–17622; and *Methods in Enzymology*, "Guide to Protein Purification", M. Deutscher, ed. Vol. 182 (1990). The recombinant cells are grown and the MHC polypeptide is expressed. The purification protocol will depend upon whether the MHC polypeptide is expressed intracellularly, into the periplasm, or secreted from the cell. For intracellular expression, the cells are harvested, lysed, and the MHC polypeptide is recovered from the cell lysate (Sambrook et al., supra.). Periplasmic MHC polypeptide is released from the periplasm by standard techniques (Sambrook et al., supra.). If the MHC polypeptide is secreted from the cells, the culture medium is harvested for purification of the secreted protein. The medium is typically clarified by centrifugation or filtration to remove cells and cell debris.

The MHC polypeptides can be concentrated by adsorption to any suitable resin such as, for example, CDP-Sepharose, Asialoprothrombin-Sepharose 4B, or Q Sepharose, or by use of ammonium sulfate fractionation, polyethylene glycol precipitation, or by ultrafiltration. Other means known in the art may be equally suitable.

Further purification of the MHC polypeptides can be accomplished by standard techniques, for example, affinity chromatography, ion exchange chromatography, sizing chromatography, or other protein purification techniques used to obtain homogeneity. The purified proteins are then used to produce pharmaceutical compositions, as described below.

Modified MHC Polypeptides

The nucleotide sequences used to transfect the host cells can be modified according to standard techniques to yield MHC polypeptides with a variety of desired properties. The MHC polypeptides of the present invention can be readily designed and manufactured utilizing various recombinant DNA techniques. Many techniques are well known to those skilled in the art, and are provided in the cited references. For example, the MHC polypeptides can vary from the naturally-occurring sequence at the primary structure level by amino acid insertions, substitutions, deletions, and the like. Protein fusions may also be utilized that may confer new activities or combinations of activities on the MHC polypeptide. These modifications can be used in a number of combinations to produce the final modified MHC polypeptide chain.

The amino acid sequence variants can be prepared with various objectives in mind, including facilitating purification and preparation of the recombinant polypeptide. The modified polypeptides are also useful for modifying therapeutic half life, improving therapeutic efficacy, and lessening the severity or occurrence of side effects during therapeutic use. The amino acid sequence variants are usually predetermined variants not found in nature but exhibit the same peptide-binding and T-cell binding activity as native-sequence MHC. For instance, polypeptide fragments comprising only a portion (usually at least about 60–80%, typically 90–95%) of the primary structure may be produced. In certain preferred embodiments, the MHC polypeptides consist essentially of either the $\alpha_1$ or $\beta_1$ domain from the full-length polypeptide. Such fragments typically comprise between about 50 and about 100 amino acids. preferably between about 60 and about 90, more preferably between about 70 and about 80. Alternatively, synthetic methods may be used to prepare polypeptides. See, e.g., Merrifield (1986) *Science* 232: 341–347; Atherton et al., *Solid Phase Peptide Synthesis: A Practical Approach*, IRL Press, Oxford).

In general, modifications of the sequences encoding the MHC polypeptides is readily accomplished by a variety of well-known techniques, such as site-directed mutagenesis (see, Gillman and Smith (1979) *Gene* 8: 81–97, and Roberts, S. et al. (1987) *Nature* 328: 731–734). Most modifications are evaluated by routine screening in a suitable assay for the desired characteristic. For instance, the effect of various modifications on the ability of the polypeptide to bind peptide or affect T-cell proliferation can be easily determined using the assays described below. Modifications of other properties such as redox or thermal stability, hydrophobicity, susceptibility to proteolysis, or the tendency to aggregate are all assayed according to standard techniques.

For certain applications, the MHC cDNA coding sequences are modified to delete the transmembrane domain and express the resulting soluble MHC polypeptides. Truncation of the MHC cDNA may be performed, for example, by oligonucleotide-directed deletion mutagenesis or polymerase chain reaction. Oligonucleotide-directed in vitro mutagenesis is described, for example, by Kunkel et al. (1987) *Meth. Enzymol.* 154: 367–382. See also, *Current Protocols in Molecular Biology*, Ausubel et al., eds., Greene Publishing and Wiley-Interscience, New York (1987 and periodic supplements).

Pharmaceutical Use of MHC Polypeptides

The unglycosylated, prokaryotically-expressed MHC polypeptides of the invention can be used to form complexes with a peptide that represents an antigen associated with, for example, autoimmunity, allograft rejection or allergic responses. The components of the complex are chosen to have a desired effect on the immune system. An effective portion of an MHC polypeptide is one that comprises the antigen binding sites and sequences necessary for recognition of the MHC-peptide complex by the appropriate T cell receptor. The MHC component can be either a Class I or a Class II molecule. The association between the peptide antigen and the antigen binding sites of the MHC protein can be by covalent or by noncovalent binding.

In other embodiments the complexes may also contain an effector component which is generally a toxin or a label. The effector portion may be conjugated to either the MHC-encoded protein or to the autoantigenic peptide. Production and use of complexes are disclosed in U.S. Pat. No. 5,130, 297, supra.

Peptide Antigens

The antigenic peptides used in the complexes of the invention are are at least about 8 residues in length, usually at least about 10 residues, more usually at least about 12. Usually, the maximum length is about 30 residues, more usually about 25, and often less than 20. The length of peptides capable of binding an MHC molecule, however, can vary. Thus. peptides of greater length, e.g., up to 100 residues can also be used in the complexes. Usually, the peptides will be less than about 50 residues in length, preferably less than about 30.

The antigenic proteins or tissues for a number of immunopathologies are known. For example, the complexes can be used to treat allergic responses. Examples of such conditions include food hypersensitivities such as celiac disease and crohn disease and allergic responses to ragweed, dust mites, cats, honey bee venom, and grass pollen. For a review of allergic diseases suitable for treatment using the methods of the present invention see, O'Hehir, et al. *Ann. Rev. Immunol.*, 9:67–95 (1991).

In experimentally induced autoimmune diseases, antigens involved in pathogenesis have been characterized: in arthritis in rat and mouse, native type-II collagen is identified in collagen-induced arthritis, and mycobacterial heat shock protein in adjuvant arthritis (Stuart et al. (1984), *Ann. Rev. Immunol.* 2: 199–218; van Eden et al. (1988), *Nature* 331: 171–173); thyroglobulin has been identified in experimental allergic thyroiditis (EAT) in mouse (Maron et al. (1988), *J. Exp. Med.* 152: 1115–1120); acetyl choline receptor (AChR) in experimental allergic myasthenia gravis (EAMG) (Lindstrom et al. (1988), *Adv. Immunol.* 42: 233–284); and myelin basic protein (MBP) and proteolipid protein (PLP) in experimental allergic encephalomyelitis (EAE) in mouse and rat (See Acha-Orbea et al. (1989)*Ann. Rev. Immunol.* 7: 377–405). In addition, for example, target antigens have been identified in humans: type-II collagen in human rheumatoid arthritis (Holoshitz et al. (1986) *Lancet* ii: 305–309); and acetyl choline receptor in myasthenia gravis (Lindstrom et al. (1988) supra).

It is believed that the presentation of antigen by the MHC glycoprotein on the surface of antigen-presenting cells (APCS) occurs subsequent to the hydrolysis of antigenic proteins into smaller peptide units. The location of these smaller segments within the antigenic protein can be determined empirically. These segments are thought to be 8–18 residues in length, and contain both the agretope (recognized by the MHC molecule) and the epitope (recognized by T cell receptor on the T-helper cell). The epitope itself is a contiguous or non-contiguous sequence of 5–6 amino acids which recognizes the antigen-specific receptor of T-helper cells. The agretope is a continuous or non-contiguous sequence which is responsible for the association of the peptide with the MHC proteins.

The empirical process of determining the relevant 8–18 amino acid subunits is illustrated using the alpha subunit of the acetylcholine receptor of skeletal muscle. In myasthenia gravis (MG) an autoimmune response is directed to a region of this subunit. A loss of the acetyl choline receptors on the postsynaptic membrane of the neuromuscular junction causes the MG symptoms.

In MG, autoantibodies against the alpha subunit of the acetylcholine receptor (AChR) are associated with the autoimmune response directed at the AChR. Eighty five percent of MG patients have autoantibodies reactive with the alpha subunit. Of these, 60% have antibodies that bind to a peptide segment of the alpha subunit called the main immunogenic region (MIR) which is located between residues 60 and 80 (Tzartos and Lindstrom, *Proc. Natl. Acad. Sci. USA* (1980) 77: 755). The peptide segments recognized by autoreactive human T cells also are located on the alpha subunit (Hohlfeld et al., *Proc. Natl. Acad. Sci. USA* (1987) 84: 5379–5383. The epitopes recognized by these T cells lie between residues 1–30, 125–147, 169–181, 257–271 and 351–368. In addition, in humans the AChR peptides 195–212 and 257–269 have been partially characterized as epitopes in myasthenia gravis patients of the HLA-DR5 and HLA-DR3, DQw2 MHC haplotypes, respectively (see Acha-Orbea (1989) supra).

The peptides carrying agretopes permitting presentation of the epitopes associated with alpha subunit of this receptor are readily determined. For example, determination of the appropriate peptides in a mouse model is carried out as follows.

Strains of mice which, when immunized with *Torpedo californicus* AChR develop a disease with many of the features of human myasthenia gravis, are used as model. MHC Class II glycoproteins are isolated from spleen cells of mice of this strain using lectin and monoclonal antibody affinity supports. The purified MHC Class II proteins are incorporated into phosphoiipid vesicles by detergent dialysis. The resultant vesicles are then allowed to fuse to clean glass cover slips to produce on each a planar lipid bilayer containing MHC molecules (Brian and McConnell, *Proc. Natl. Acad. Sci. USA* (1984) 81: 6159.

One cover slip containing MHC Class II molecules embedded in the adherent planar lipid membrane is placed in each well of several 24-well culture plates. Each one of the approximately 40 overlapping 20-residue synthetic peptides corresponding to the alpha subunit sequence and containing one or more radiolabeled amino acid residues (prepared as described below) is placed in a well with cover slip and PBS and allowed to incubate several days. The extent of binding of peptide in the MHC Class II glycoprotein antigen binding site is measured by the amount of radio-activity incorporated into the MHC Class II-planar lipid membrane on the cover slip versus planar lipid membrane alone. Specific incorporation of radioactivity indicates that the bound peptide contains an agretope (MHC Class II peptide binding site) of one of the several species of MHC Class II molecules present in the planar lipid membrane. In this way, the set of agretopes for the alpha subunit of AChR is defined for the mouse strain that displays the symptoms of MG upon immunization with AChR or purified alpha subunit.

Next, each of the alpha subunit synthetic peptide segments that contain an agretope is again incorporated into the antigen binding site of isolated MHC Class II proteins embedded in planar lipid membranes on cover slips. One cover slip is added to each well of a 24-well culture plate, and spleen cells from mice immunized against ACHR (and from which strain the adherent MHC Class II proteins were isolated) are added to each well. T cell hybridoma proliferation, as measured by tritiated thymidine uptake into DNA, indicates that the MHC Class II protein-bound peptide contains both an agretope and an epitope for binding to the T cell. Activation of T cell clones is determined by measuring IL-3 production (see, Quill et al., supra).

The Dupont apparatus and technique for rapid multiple peptide synthesis (RAMPS) is used to synthesize the members of a set of overlapping (10 residue overlap), 20-residue peptides from the alpha subunit of *Torpedo californicus* AChR. One or more radioactive amino acids is incorporated into each synthetic peptide. The pentafluorphenyl active esters of side chain-protected, FMOC amino acids are used to synthesize the peptides, applying standard stepwise solid phase peptide synthetic methods, followed by standard side chain deprotection and simultaneous release of the peptide amide from the solid support.

Alternatively the overlapping sequences which include the putative segments of 8–18 amino acids of the antigenic protein, such as acetylcholine receptor protein, can be synthesized on the method of Geysen, H. M., et al. *J. Immun.*

*Meth.* (1987) 102: 274. The synthesized radiolabeled peptides are tested by incubating them individually (on the plates) with purified MHC proteins that have been formulated into lipid membrane bilayers as above.

In multiple sclerosis (MS), which results in the destruction of the myelin sheath in the central nervous system, myelin basic protein (MBP), the major protein component of myelin is the principal autoantigen. Pertinent segments of the MBP protein are also determined empirically, using a strain of mice which develops experimental allergic encephalitis (EAG) when immunized with bovine myelin basic protein.

Systemic lupus erythematosus (SLE) has a complex symptomology, but results from an autoimmune response to red blood cells. Peptides which are the antigenic effectors of this disease are found in the proteins on the surface of red blood cells.

Rheumatoid arthritis (RA) is a chronic inflammatory disease resulting from an immune response to proteins found in the synovial fluid.

Insulin-dependent diabetes mellitus (IDDM) results from autoimmune attack on the beta cells within the Islets of Langerhans which are responsible for secretion of insulin. Circulating antibodies to Islets cells surface antigens and to insulin are known to precede IDDM. Critical peptides in eliciting the immune response in IDDM are believed to be portions of the insulin sequence and the beta cell membrane surface proteins.

The relevant antigenic peptide subunits, as they are relatively short, can readily be synthesized using standard automated methods for peptide synthesis. In the alternative, they can be made recombinantly using isolated or synthetic DNA sequences, although this is not the most efficient approach for peptides of this length.

Thus, in summary, a set of labeled test peptides is prepared, and those which bind to MHC in planar lipid membranes containing MHC proteins are shown to contain the agretope.

The identified peptides are then prepared by conventional solid phase synthesis and the subset which contain epitopes for the disease-inducing helper T cell clones is determined by incubation of the candidate peptides with murine antigen-presenting cells (APC) (or with isolated MHC complex) and spleen or lymph node T cells from mice immunized with the full length protein. Successful candidates will stimulate T cell proliferation in this system. This second, smaller, subset represents the suitable peptide component.

Formation of the Complex

The elements of the complex can be associated by standard means known in the art, as described in U.S. Pat. No. 5,130,297, supra. The antigenic peptides can be associated noncovalently with the pocket portion of the MHC protein by, for example, mixing the two components. Excess peptide can be removed by any of a number of standard procedures, such as ultrafiltration or dialysis. The peptides can also be covalentdy bound using standard procedures by, for example, photo affinity labelling, (see, e.g., Hall et al., *Biochemistry* 24: 5702–5711 (1985). Alternatively, the peptide can be covalently bound to the MHC component by expressing the peptide and MHC component from a single polynucleotide sequence. For example, the peptide can be covalently attached to the MHC component through a flexible peptide linker (see, e.g., Kozono et al. *Nature* 369:151–154 (1994)).

Assessment of the Complex

The complexes formed using MHC polypeptides of the invention can be assayed using an in vitro system or using an in vivo model. In the in vitro system, the complex is incubated with peripheral blood T cells from subjects immunized with, or showing immunity to, the protein or antigen responsible for the condition associated with the peptide of the complex. The successful complexes will induce anergy in syngeneic T cells and prevent proliferation of the T cells even upon stimulation with additional antigen.

In the in vivo system, T cells that proliferate in response to the isolated epitope or to the full length antigen in the presence of APC are cloned. The clones are injected into histocompatible animals that have not been immunized, in order to induce the autoimmune disease. The relevant complex should ameliorate or eliminate the symptoms of the disease.

Either of the types of complexes, i.e., with or without the effector component, may be used. In one mode the treatment is two-fold. The individual is treated with the complex of prokaryotically-expressed, MHC-encoded antigen-presenting protein containing an effective portion of the antigenic peptide to down-regulate the immune system. Further down-regulation is achieved by treatment with the three component complex with includes the prokaryotically-expressed, MHC-encoded antigen-presenting protein, an effective portion of antigenic peptide which is specific for the autoimmune disease being treated, and an effector component. In addition, panels of complexes may be used for treatment. For example, if it is suspected that more than one peptide of an antigen is involved in the autoimmune response, and/or if it is suspected that more than one antigen is involved, the individual may be treated with several complexes selected from a panel containing the effective portion of the appropriate prokaryotically-expressed, MHC-encoded antigen-presenting polypeptides, and effective portions of antigenic peptides; these may be with or without effector components.

Administration of a labeled complex permits identification of those portions of the immune system involved in the disease, in diagnostic applications.

Selection of the MHC Complexes for Therapy and/or Diagnosis

In order to select the MHC complexes that are to be used in the diagnosis or treatment of an individual for a particular disease, the type of MHC antigens that are involved in the presentation of the antigen are identified. The following discussion describes the identification of antigen associated with autoimmune disease, but one of skill will recognize that the same general approach can be used for other diseases, such as allergies.

Specific autoimmune dysfunctions are correlated with specific MHC types. Methods for identifying which alleles, and subsequently which MHC encoded polypeptides, are associated with an autoimmune disease are known in the art. A method described in EP 286447 is suitable. In this method several steps are followed. First, the association between an MHC antigen and the autoimmune disease is determined based upon genetic studies. The methods for carrying out these studies are known to those skilled in the art, and information on all known HLA disease associations in humans is maintained in the HLA and Disease Registry in Copenhagen. The locus encoding the polypeptide associated with the disease is the one that would bear the strongest association with the disease.

Second, specific alleles encoding the disease associated with MHC antigen/polypeptide are identified. In the identification of the alleles, it is assumed that the susceptibility allele is dominant. Identification of the Allen is accomplished by determining the strong positive association of a specific subtype with the disease. This may be accomplished in a number of ways, all of which are known to those skilled in the art. For example, subtyping may be accomplished by mixed lymphocyte response (MLR) typing and by primed lymphocyte testing (PLT). Both methods are described in Weir and Blackwell, eds., *Handbook of Experimental Immunology*. It may also be accomplished by analyzing DNA restriction fragment length polymorphism (RFLP) using DNA probes that are specific for the MHC locus being examined. E.g., Nepom (1986) *Annals N.Y. Acad. Sci.* 475: 1. Methods for preparing probes for the MHC loci are known to those skilled in the art. See, e.g., Gregersen et al. (1986), *Proc. Natl. Acad. Sci. USA* 79: 5966; Weissman et al. in *Medicine in Transition: the Centennial of the University of Illinois College of Medicine* (E. P. Cohen, ed., 1981).

The most complete identification of subtypes conferring disease susceptibility is accomplished by sequencing of genomic DNA of the locus, or cDNA copies of mRNA transcribed within the locus. The DNA that is sequenced includes the section encoding the hypervariable regions of the MHC encoded polypeptide. Techniques for identifying specifically desired DNA with a probe, for amplification of the desired region are known in the art, and include, for example, the polymerase chain reaction (PCR) technique.

Once the allele that confers susceptibility to the specific autoimmune disease is identified, the polypeptide encoded within the allele is also identifiable, i.e., the polypeptide sequence can be deduced from the sequence of DNA within the allele encoding it. The MHC antigen complexes of the invention used for diagnosis and/or therapy are derived from the effective portion of the MHC antigen associated with the autoimmune disease state and from an autoimmune antigen associated with the same disease state.

As an example, over 90% of rheumatoid arthritis patients have a haplotype of DR4(Dw4), DR4(Dw14) or DR1. It is also known that a target antigen in human rheumatoid arthritis is type-II collagen. Hence, the complexes of the invention used for treatment or diagnosis of an individual with rheumatoid arthritis would include those containing a polypeptide derived from the DR4(Dw4), DR1 and/or DR4 (Dw14) which is capable of antigen presentation for disease induction, or incapable of antigen presentation for disease suppression, complexed with an effective portion of type-II collagen.

As used herein, the term "individual" encompasses all mammals and all vertebrates which possess basically equivalent MHC systems.

Formulation and Administration

If the transmembrane region of the MHC subunit is included, the complexes formed using prokaryotically-expressed MHC polypeptides of the invention are conveniently administered after being incorporated into lipid monolayers or bilayers. Typically liposomes are used for this purpose but any form of lipid membrane, such as planar lipid membranes or the cell membrane of a cell (e.g., a red blood cell) may be used. The complexes are also conveniently incorporated into micelles. The data presented in Example 2, below, shows that MHC-peptide complexes comprising dimeric MHC molecules exist primarily as aggregates.

Liposomes can be prepared according to standard methods, as described below. However, if the transmembrane region is deleted, the complex can be administered in a manner conventionally used for peptide-containing pharmaceuticals.

Administration is systemic and is effected by injection, preferably intravenous, thus formulations compatible with the injection route of administration may be used. Suitable formulations are found in *Remington's Pharmaceutical Sciences*, Mack Publishing Company, Philadelphia, Pa., 17th ed. (1985). A variety of pharmaceutical compositions comprising complexes of the present invention and pharmaceutically effective carriers can be prepared. The pharmaceutical compositions are suitable in a variety of drug delivery systems. For a brief review of present methods of drug delivery, see, Langer, *Science* 249: 1527–1533 (1990).

In preparing pharmaceutical compositions using the prokaryotically-expressed, unglycosylated MHC polypeptides of the present invention, it is frequently desirable to modify the complexes of the present invention to alter their pharmacokinetics and biodistribution. For a general discussion of pharmacokinetics, see, *Remington's Pharmaceutical Sciences*, supra, Chapters 37–39. A number of methods for altering pharmacokinetics and biodistribution are known to one of ordinary skill in the art (see, e.g., Langer, supra). For example, conjugation to soluble macromolecules, such as proteins, polysaccharides, or synthetic polymers, such as polyethylene glycol, is effective. Other methods include protection of the complexes in vesicles composed of substances such as proteins, lipids (for example, liposomes), carbohydrates, or synthetic polymers.

Liposomes of the present invention typically contain the MHC-peptide complexes positioned on the surface of the liposome in such a manner that the complexes are available for interaction with the T cell receptor. The transmembrane region is usually first incorporated into the membrane at the time of forming the membrane. The liposomes can be used to target desired drugs (e.g., toxins or chemotherapeutic agents) to particular autoreactive T cells. Alternatively, the complexes embedded in the liposome may be used to induce anergy in the targeted cells.

A variety of methods are available for preparing liposomes, as described in, e.g., Szoka et al., *Ann. Rev. Biophys. Bioeng.* 9: 467 (1980), U.S. Pat. Nos. 4,235,871, 4,501,728 and 4,837,028.

Micelles are also commonly used in the art to increase solubility of molecules having nonpolar regions. One of skill will thus recognize that micelles are useful in compositions of the present invention. Micelles comprising the complexes of the invention are prepared according to methods well known in the art (see, e.g., *Remington's Pharmaceutical Sciences*, supra, Chap. 20). Micelles comprising the complexes of the present invention are typically prepared using standard surfactants or detergents.

Common surfactants well known to one of skill in the art can be used in the micelles of the present invention. Suitable surfactants include sodium laureate, sodium oleate, sodium lauryl sulfate, octaoxyethylene glycol monododecyl ether, octoxynol 9 and PLURONIC F-127®(Wyandotte Chemicals Corp.). Preferred surfactants are nonionic polyoxyethylene and polyoxypropylene detergents compatible with IV injection such as, TWEEN-80®, PLURONIC F-68®, n-octyl-β-D-glucopyranoside, and the like. In addition, phospholipids, such as those described for use in the production of liposomes, may also be used for micelle formation.

Since the MHC subunits of the present invention comprise a lipophilic transmembrane region and a relatively hydrophilic extracellular domain, mixed micelles are formed in the presence of common surfactants or phospholipids and the subunits. The mixed micelles of the present invention may comprise any combination of the subunits, phospholipids and/or surfactants. Thus, the micelles may comprise subunits and detergent, subunits in combination with both phospholipids and detergent, or subunits and phospholipid.

For pharmaceutical compositions which comprise the complexes of the present invention, the dose will vary according to, e.g., the particular complex, the manner of administration, the particular disease being treated and its severity, the overall health and condition of the patient, and the judgment of the prescribing physician. Dosage levels for murine subjects are generally between about 10 μg and about 500 μg. A total dose of between about 50 μg and about 300 μg, is preferred. For instance, in treatments provided over the course of a disease, three 25 μg or 100 μg doses are effective. Total dosages range between about 0.015 and about 15 μg/kg, preferably about 0.15 to about 10 μg/kg.

The pharmaceutical compositions are intended for parenteral, topical, oral or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, and capsules.

Preferably, the pharmaceutical compositions are administered intravenously. Thus, this invention provides compositions for intravenous administration which comprise a solution of the complex dissolved or suspended in an acceptable carrier, preferably an aqueous carrier. A variety of aqueous carriers may be used, e.g., water, buffered water, 0.4% saline, and the like. For instance, phosphate buffered saline (PBS) is particularly suitable for administration of soluble complexes of the present invention. A preferred formulation is PBS containing 0.02% TWEEN-80. These compositions may be sterilized by conventional, well-known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the complex can vary widely, i.e., from less than about 0.05%, usually at or at least about 1% to as much as 10 to 30% by weight and will be selected primarily by fluid volumes, viscosities, etc., in accordance with the particular mode of administration selected. Preferred concentrations for intravenous administration are about 0.02% to about 0.1% or more in PBS.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient.

For aerosol administration, the complexes are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1%–20% by weight of the composition, preferably 0.25–5%. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided compounds and surfactant. The ingredients are thus maintained at an elevated pressure until released by action of the valve.

The compositions containing the complexes can be administered for therapeutic, prophylactic, or diagnostic applications. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient. As discussed above, this will typically be between about 0.5 mg/kg and about 25 mg/kg, preferably about 3 to about 15 mg/kg.

In prophylactic applications, the complexes of the invention are administered to a patient susceptible to or otherwise at risk of a particular disease. Such an amount is defined to be a "prophylactically effective dose." In this use, the precise amounts again depend on the patient's state of health and weight. The doses will generally be in the ranges set forth above.

In diagnostic applications, compositions containing the appropriate complexes or a cocktail thereof are administered to a patient suspected of having an autoimmune disease state to determine the presence of autoreactive T cells associated with the disease. Alternatively, the efficacy of a particular treatment can be monitored. An amount sufficient to accomplish this is defined to be a "diagnostically effective dose." In this use, the precise amounts will depend upon the patient's state of health and the like, but generally range from 0.01 to 1000 mg per dose, especially about 10 to about 100 mg per patient.

Kits can also be supplied for therapeutic or diagnostic uses. Thus, the complexes of the present invention may be provided, usually in a lyophilized form in a container. The complexes, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of complex and usually present in total amount of at least about 0.001% wt. based again on the protein concentration. Frequently, it will be desirable to include an inert extender or excipient to dilute the active ingredients, where the excipient may be present in from about 1 to 99% wt. of the total composition. Where an antibody capable of binding to the complex is employed in an assay, this will usually be present in a separate vial. The antibody is typically conjugated to a label and formulated according to techniques well known in the art.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described.

EXAMPLE 1

Construction of Bacterial Expression Vector for MHC class II

Strategy. MHC class II molecules were expressed in *E. coli* using an expression vector derived from that described by Squires et al. (*J. Biol. Chem.* (1988) 263: 16297–16302). The MHC gene was inserted into a modified expression vector that contains a T7 promoter to drive expression of the inserted gene. Both full-length and truncated (ΔTM) MHC genes were expressed. The nucleotide sequences coding for the transmembrane and cytoplasmically exposed regions of the MHC polypeptides were deleted in the ΔTM constructs (See SEQ. ID. Nos. 11 and 13). SEQ. ID. No. 11 shows the DNA sequence corresponding to the mature full-length form of the HLA DR2-Dw2 α-chain and SEQ. ID. No. 13 shows the HLA DR2-Dw2 β-chain. The ΔTM constructs were made by deleting the region between positions 577 and 690 of the α-chain and the region between positions 595 and 714 in the β-chain respectively.

Reagents and Materials. Oligonucleotides were synthesized on an Applied Biosystems 392 DNA synthesizer using β-cyanoethyl phosphoramidite chemistry and were purified using Applied Biosystems OPC cartridges per manufacturers instructions. Plasmids pEI3a and pET11b, which contain the bacteriophage T7 promoter, were purchased from Novagen. Plasmid pUC19 and all restriction enzymes and DNA modifying enzymes were purchased from New England Biolabs.

*E. coli* K-12 strain W3110 was obtained from the ATCC. The cell line GMO3107 (source of the MHC sequences) was obtained from the National Institute of General Medical Sciences (NIGMS) repository at the Coriell Institute for Medical Research. GMO3107 is an EBV transformed human cell line that expresses high levels of the DR2-Dw2 heterodimer complex on its surface.

Construction of an *E. coli* Expression Plasmid. Expression plasmids for MHC class II molecules were constructed from pET3a as follows.

pET3a was digested with EcoRI. blunt-ended with DNA Polymerase I (Klenow fragment) and digested with EcoRV. The vector was recircularized, destroying both restriction sites, to generate plasmid p26404.

Plasmid p26405 was derived from p26404 as follows. First, p26404 was digested with BamHI and the ends were filled-in with DNA polymerase I (Klenow) to generate blunt ends. A synthetic linker of sequence: 5'. . . CGGAATT-CCG . . . 3' (SEQ. ID. No. 15) was introduced into the destroyed BamHI site, thus replacing it with a new EcoRI site.

Plasmid p26411 was generated by digestion of p26405 with NdeI and EcoRI and insertion of a synthetic linker sequence:

This linker provides the first 14 codons of the phi-10 open reading frame (coupler), and has a BamHI site located in the proper reading frame for subsequent expression of an inserted MHC gene. Downstream of the BamHI site is a HindIII cloning site that together with the EcoRI site provides two downstream sites for directional cloning of inserts.

To facilitate cloning, one of the BamHI sites in p26411 was destroyed to generate plasmid p27305. p26411 was digested with EcoRI+PstI and the 3387bp fragment recovered. p26411 was also digested with BamHI and PstI and the 891bp fragment was recovered. A synthetic linker of sequence:

```
5'...AATTCCTACGTA...3'      (SEQ. ID. No. 3)
3'...GGATGCATCTAG...5'      (SEQ. ID. No. 4)
``` was made and ligated with the two fragments of p26411 to generate p27305. The linker has both EcoRI and BamHI cohesive ends, but will regenerate only the EcoRI site upon ligation. Additionally, it carries a SnaBI (blunt) cloning site for future downstream manipulations.

Plasmid p27313 incorporates a copy of the lacI$^q$ repressor protein onto p27305 to control unwanted transcription of the target gene prior to induction, p27305 was digested with BamnHI and PstI and a 917 bp fragment recovered. Plasmid pET11b was similarly treated and a 4608 bp fragment recovered. Ligation of the two fragments yielded the final form of the expression plasmid, p27313.

Cloning of DR2-Dw2 Alpha and Beta Chain Genes. Poly-A$^+$ mRNA was prepared from $5.0 \times 10^7$ viable GMO3107 cells using a Fast Track kit (Invitrogen), following the manufacturer's instructions.

cDNA was prepared from 25 ng of poly-A+mRNA using a Clontech first-strand cDNA synthesis kit, following the manufacturer's instructions.

Sequence information for the human HLA DR2-Dw2 α (dra) (Lee et al. (1987) *Proc. Natl. Acad. Sci. USA* 84: 4591–4597) and β (DRB5*0101) (Lee et al. (1984) *Nature* 299: 750–752) chain genes were obtained from the GenBank database. Primers were designed for PCR amplification of either the mature gene product or a truncated (ΔTM) form of each chain. The "top strand" primer of each chain included a portion of the phi-10 gene corresponding to the translational coupler used in the *E. coli* expression system.

```
5'...TATG GCT AGC ATG ACT GGT GGA CAG CAA ATG GGT CGG GAT CCG AAGCTT AG...3'    (SEQ. ID. No. 1)

3'...AC CGA TCG TAC TGA CCA CCT GTC GTT TAC CCA GCC CTA GGC TTCGAA TCTAA...5'   (SEQ. ID. No.2)
```

```
DR2-Alpha chain:

"Top strand"
5'..CGGGATCCGATCGTGGAGGATGATTAAATGATCAAAGAAGAACATGTGATCATC..3'      (SEQ. ID. No. 5)

Full-length "bottom strand"
5'...GTCGAATTCTTACAGAGGCCCCCTGCGTT...3'                              (SEQ. ID. No. 6)

Truncated (ΔTM) "bottom strand"
5'...ATCGAATTCAGTTCTCTGTAGTCTCTGGGAG...3'                            (SEQ. ID. NO. 7)

Dr2-Beta Chain:

"Top strand"
5'...CGGGATCCGATCGTGGAGGATGATTAAATGGGGGACACCCGACCACGTT...3'          (SEQ. ID. No. 8)

Full-length "bottom strand"
5'...GTCGAATTCTCAGCTCACGAGTCCTGTTGG...3'                             (SEQ. ID. No. 9)

Truncated (ΔTM) "bottom strand"
5'...ATCGAATTCACTTGCTCTGTGCAGATTCAGA...3'                            (SEQ. ID. No. 10)
```

Following amplification, the PCR products were digested with BamHI and EcoRI and subcloned into the plasmid pUC9 which had been similarly treated. Recombinant clones were identified and sequenced. The plasmids containing recombinant α- and β-chain genes were designated p26416 and p26417 respectively. Sequence analysis of the a chain revealed a point mutation (G to T) at base 649 of the published sequence. This mutation results in a valine to leucine substitution at residue 217 of the full length mature gene product. No deviations from the published sequence were observed for the β-chain.

Full-length Expression Constructs. Plasmids p26416 and p26417 were treated with BamnHI and EcoRI. Fragments corresponding to the α- and β-chains were subcloned into the expression vector p27313. Recombinant clones were identified by restriction analysis and given the designations p27317 (α-chain) and p27316 (β-chain).

ΔTM Expression Constructs. PCR amplification of truncated α- and β-chain genes was performed using the PCR primer pairs previously described. The plasmids p26416 and p26417 were used as target DNA for the α- and β-chain, respectively. The PCR products were treated with BamHI and EcoRI and ligated into plasmid p27316 which had been treated with the same enzymes to remove the full-length β-chain. The resulting plasmids were designated p26495 (α-ΔTM) and p26496 (β-ΔTM).

EXAMPLE 2

Expression of MHC Class II Molecules in *E. coli*

Construction of Host Strain W3110/DE3. *E. coli* strain W3110 was made lysogenic for the phage lambda-DE3 (which carries a copy of the T7 RNA polymerase gene) using the DE3 lysogenization kit from Novagen, following the manufacturer's instructions.

Induction of Recombinant Clones. Plasmids p27316, p27317, p26495 and p26496 were transformed into the host strain W3110/DE3.

Cultures were grown at 37° C. in LB containing 0.4% glucose and 100 μg/ml ampicillin. Cells were induced in mid-log growth by addition of isopropyl-β-b-D-thiogalactopyranoside (IPTG) (0.4 mM final concentration) and allowed to grow at 37° C. Periodic samples were taken and chilled on ice prior to processing.

Cells were harvested by centrifugation at 5000×g at 4° C. for 10 minutes. Cells were resuspended in TE (10 mM Tris-Cl, 1 mM EDTA pH 8.0) in a volume appropriate to yield 0.02 $OD_{600}/\mu l$. Reduced samples were prepared by adding equal volumes of cell suspension and 2×SDS-sample buffer containing 0.3M 2-mercaptoethanol and boiling for 5 minutes. Ten microliters of sample were applied to a 12% SDS-gel and following electrophoresis proteins were visualized with Coomasie Brilliant Blue staining.

For solubility testing, 200 μl of cell suspension was sonicated with a micro-tip at a setting of 4 for three 10-second bursts on ice. Insoluble material was separated from soluble material by centrifugation for 10 minutes at 12,000×g at 4° C. The insoluble material (inclusion body) was washed once with 500 μl of cold TE and respun. The pellet was then aspirated and dissolved in 400 μl of 1×SDS-sample buffer containing 0.3M 2-mercaptoethanol and boiled.

Purification of rDR2 α and β chains. Recombinant DR2 α and β chains with and without the transmembrane region were purified by preparative electroelution as generally described in Passmore et al *J. Inmmunol. Meth.* 155:193–200 (1992). Inclusion body preparations in 8M urea and 10 mM DTT at a concentration of 6 mg/ml were dialyzed for 16 hours against sample buffer: 25 mM Tris-HCl, pH 6.8 and 0.25% SDS. Two mg of starting sample was loaded onto a Bio-Rad Prep Cell device containing 13.5% resolving and 4% stacking gel. Electrophoresis was performed at 40 mA constant current for the duration of elution. Fractions (3 ml) were collected starting at 360 minutes with a flow rate of 1 ml/min. Eluted fractions were analyzed for by 13.5% non-reducing SDS-PAGE followed by silver stain. Based on polyacrylamide gel analysis, α and β monomers were pooled and concentrated with an Amicon Centriprep 10 k molecular weight cut-off filtration system. The final monomer preparations were dialyzed against PBS containing 0.01% Tween-80 and 0.02% azide. The yield was calculated by Lowry assay, with a typical recovery ranging between 15–30% of the loaded protein. MHC polypeptides purified by this method were free of any detectible contaminants.

Results. Clones of the mature full length α- and β-chains of DR2-Dw2 as well as truncated forms of each lacking the putative transmembrane and cytoplasmic tail regions have been constructed and inserted into a T7 expression vector for expression in *E. coli*.

The α-chain clone used herein contains a nucleotide substitution at base 649, compared to the published sequence. This difference results in the substitution of a leucine residue in place of a valine residue at amino acid 217 of the full length product. This residue is within the transmembrane portion of the molecule and is therefore not present in the ΔTM construct. Because of the conservative nature of the leucine for valine substitution, and its positioning within the transmembrane region, the mutation was not considered a significant hinder to further experiments with regard to peptide binding and interaction with T-cells.

Induction of both full-length and truncated constructs in W3110/DE3 resulted in the substantial accumulation of protein at or near the expected size as evaluated by SDS-PAGE. Below is a summary of the lengths and expected molecular weights for each of the four proteins evaluated:

| Protein | Residues | Expected $M_r$ |
| --- | --- | --- |
| Alpha Full-length | 229 | 25971 |
| Beta Full-length | 237 | 27035 |
| Alpha ΔTM | 192 | 22174 |
| Beta ΔTM | 198 | 23024 |

Following sonication of the cells and separation of the soluble and insoluble fractions by centrifugation, the target gene products were located in the soluble (inclusion body) fraction in all constructs.

$NH_2$-terminal amino acid sequencing of the first five residues of the DR2-Dw2 alpha chain full length and ΔTM products matched exactly the predicted amino acid sequence for the natural product except that a methionine residue was found in the first position, presumably due to its incomplete removal in vivo by E. coli. $NH_2$-terminal sequence analysis of the first five residues of the two β-chain gene products matched exactly the expected mature sequence for this chain with no methionine present in the first position.

The E. coli-expressed α- and β-chains bind peptide as well as isolated chains of the naturally derived material. Thus, the denatured single chains are able to achieve some level of conformation (without complex refolding procedures) that enables them to bind peptide.

While complex refolding steps do not appear necessary, improvements in binding efficiency might be realized following controlled renaturation of the single chain moieties.

EXAMPLE 3

Binding of Antigenic Peptide to Recombinant MHC Polypeptide

Purified chains at a concentration of 200 μg/ml and DR2 dimers at a concentration of 400 μg/ml were incubated with radiolabeled MBP(83–102)$y^{83}$ peptide or MBP(1–14) peptide at 37° C. for 96 hours. Three μg of the samples were analyzed on 13.5% polyacrylamide SDS-PAGE under non-reducing conditions. Gels were stained with silver stain, autoradiographed and radioactivity associated with each chain was counted. The percent of chains occupied with labeled peptide was calculated from the specific activity of the respective peptides.

Results presented in FIG. 1 show that rDR2β(–TM) bound maximum peptide followed by rDR2α(+TM) and rDR2β(+TM). The rDR2α(–TM) showed no significant binding of MBP(83–102)$Y^{83}$ peptide. In addition, recombinant chains showed increased binding as compared to equimolar amount of DR2 native heterodimer. The results were reproducible in 4 different experiments. The specificity of the peptide binding was demonstrated by incubating the chains with an equivalent amount of another epitope from the same myelin basic protein, MBP(1–14). In all cases, the binding of MBP(1–14) was insignificant.

Figure 2:
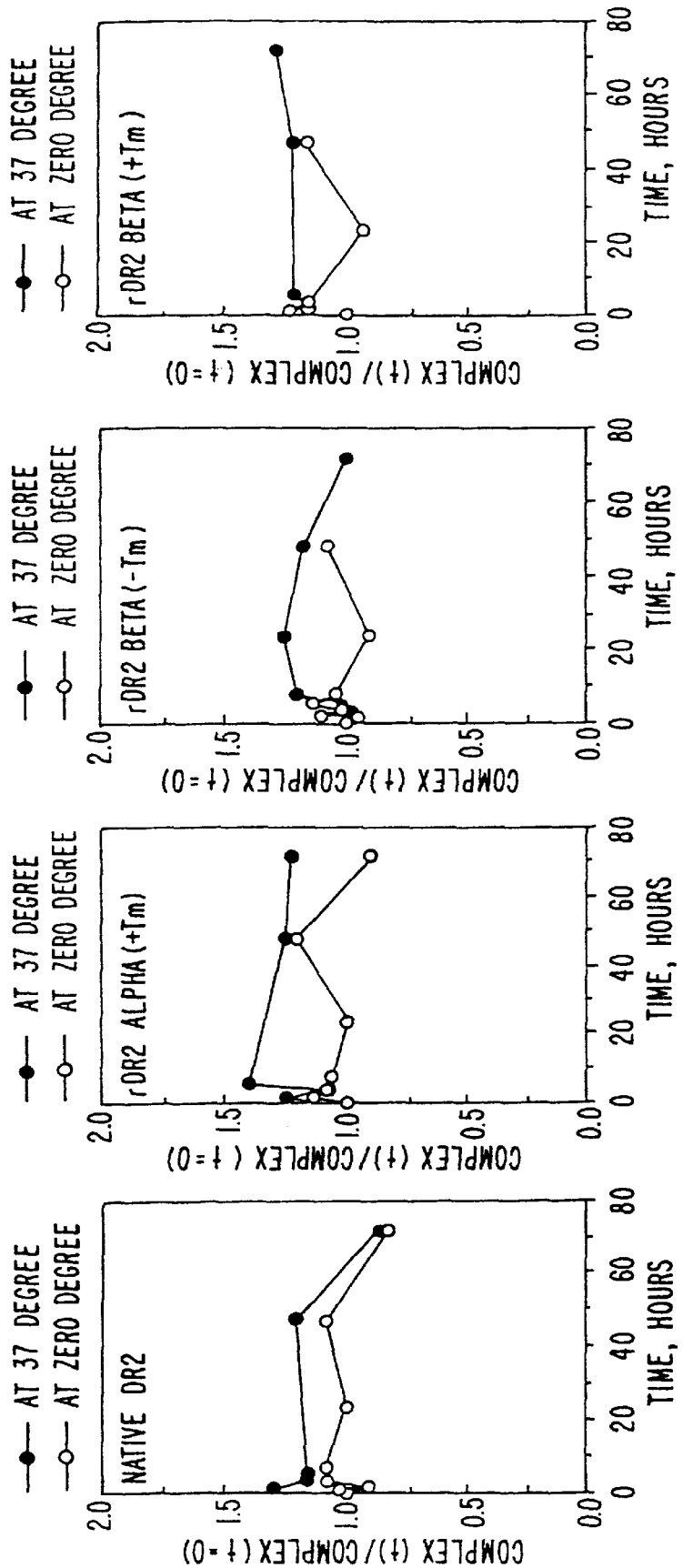
FIG. 2 shows the stability of recombinant DR2-peptide complexes.
Figure 3A:
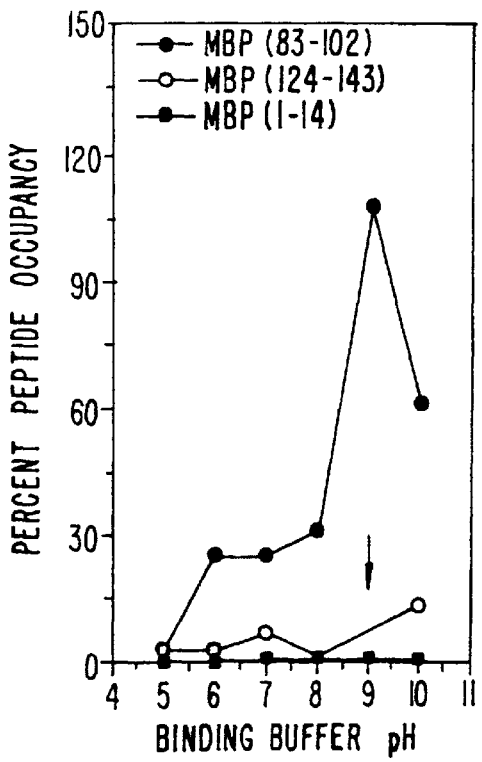
FIG. 3 shows optimum pH for maximum binding of MBP peptids to purified recombinant DR2 polypeptide chains.
Figure 3B:
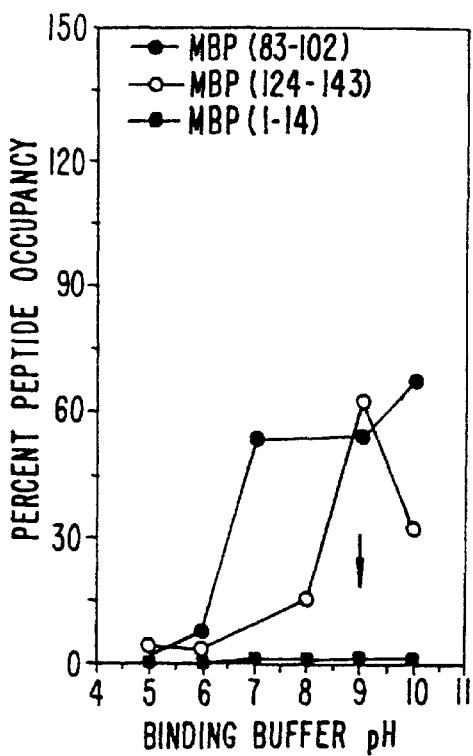
Figure 3C:
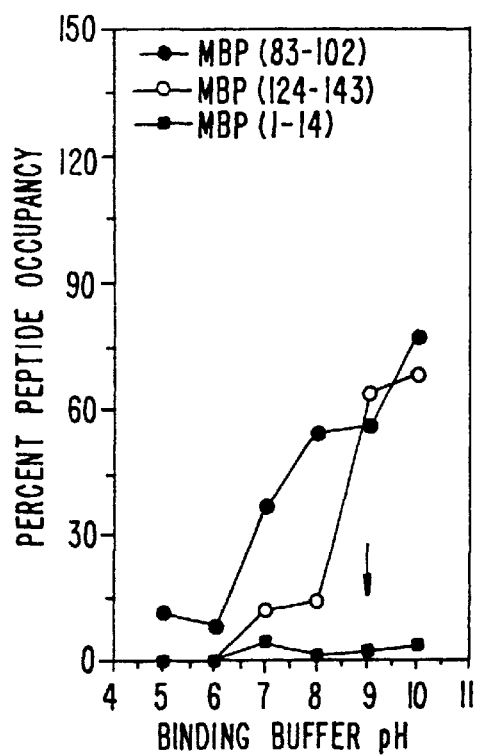
Figure 3D:
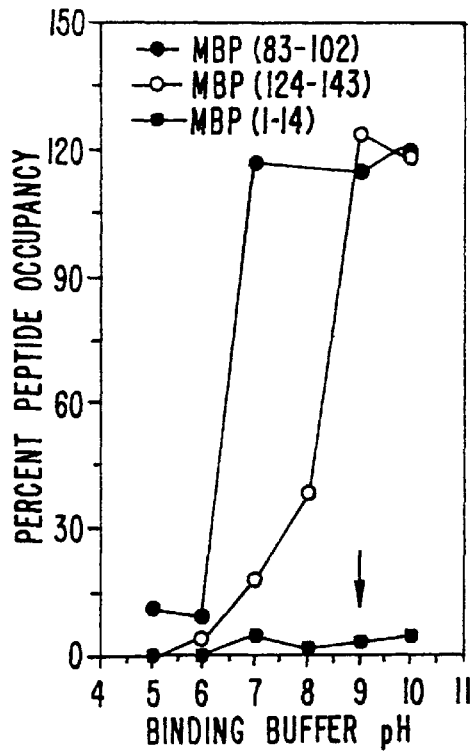

Association and Dissociation Kinetics of rDR2 Chains with Radiolabeled Peptides. The on rate kinetics of binding was measured similarly as described above. Chains at a concentration of 200 μg/ml were incubated at 37° C. with labeled peptide. At various times, 15 μl of sample was removed, chilled to 4° C. and analyzed on 13.5% SDS-PAGE. The percent peptide occupancy was calculated from the specific activity as described above. The stability of chain-peptide complexes were compared at zero and at 37° C. (FIG. 2). Single chain-peptide complexes appeared to be as stable as the heterodimeric native DR2-peptide complexes.

EXAMPLE 4

Peptide Binding Assay with Biotinylated Antigenic Peptide

Further binding studies were carried out using the four recombinant chains, rDR2α(+TM), rDR2α(–TM), rDR2β(+TM), rDR2β(–TM), purified by conventional preparative chromatographic procedures as described above. Biotinylated-MBP (83–102)$Y^{83}$, biotinylated-MBP (124–143) and biotinylated-MBP (1–14) peptides were used for the binding assay. Recombinant chains at a concentration of 0.2 mg/ml was incubated with 50 fold molar excess of biotinylated-MBP peptides. For the quantitation of the percentage of chain occupied with the biotinylated-peptide, resulting complexes were analyzed in a plate assay using enzyme conjugated avidin system. One mg per 50 ml affinity purified L243 monoclonal antibody, polyclonal anti-alpha and polyclonal anti-beta were coated for the DR2, α and β chains (with and without transmembrane regions), respectively on a 96 well microtiter plate. The polyclonal anti-α and anti-β antibodies were purified from immunized rabbit sera on a antigen-coupled sepharose-4B column. Calibration of the assay was achieved by coating know amounts of biotinylated-BSA. After capture of complexes, unbound peptide was removed by washing, followed by incubation with avidin-alkaline phosphatase. Unbound enzyme conjugate was removed by washing, and a colorimetric substrate (Sigma 104) was added to the the detection of the enzymatic product by measuring absorbance of 405 nm.

Native HLA-DR2 has been shown to have high affinity for peptides MBP (83–102)$Y^{83}$ and MBP (124–143) and no affinity for MBP (1–14). The results presented in FIG. 3 show that purified recombinant polypeptide chains, like native heterodimers were capable of binding both MBP (83–102)$Y^{83}$ and MBP(124–143) peptides. The MBP (1–14) did not show any significant binding to any purified chain preparations. The optimum pH for maximum binding was different than native DP2 in all cases.

EXAMPLE 5

T Cell Receptor Occupancy Assay

The herpesvirus saimiri (HVS) transformed SS8T human T cell clone (provided by H. Wekerie, Max Planck Institute for Psychiatry, Munich, Germany, see, Weber et al. Proc. Natl. Acad. Sci. USA 90:11049–11053 (1993)) which recognizes MBP(83–102)$Y^{83}$ in the context of DRB5 * 0101 was cultured in RPMI 1640 medium supplemented with 2 mM L-glutamine, 100 units/ml penicillin, 100 μg/ml streptomycin, 10% fetal bovine serum (Hyclone) and 50 units/ml human IL-2 (ABI) at 37° C. Every alternate day the cells were transferred to fresh media. Based on the binding results shown in example 4, complexes of the four purified recombinant chains with MBP (83–102)$Y^{83}$ and MBP (124–143) peptides were prepared for the in vitro functional assay. Various complex preparations were added at a final concentration of 10% v/v in a microtiter tissue culture plate and the cells were added at a density of 20,000/well in 200 µl media without IL-2. After 48 hours incubation at 37° C., the supernatants were collected from each well to test for the increase in gamma-IFN level. For the detection of gamma-IFN, Nunc Maxisorb 96 well plates were coated with anti-human gamma-IFN monoclonal antibody at a concentration of 0.5 µg/well and incubated at 4° C. overnight. The wells were blocked with 0.1% BSA, and samples were incubated at room temperature for 2 hours. The standard curve was generated by using human gamma-IFN with a dilution range of 1000 , 500, 100, 50, 10, 5, 1, 0.5, 0.1 units/ml (270 units/ml=10.75 ng/ml). Rabbit anti-human gamma-IFN was then added at a concentration of 1 µg/ml and plates were incubated at room temperature for additional 2 hours. Wells were extensively washed and incubated with HRP-conjugated goat anti-rabbit at a concentration of 800 ng/ml for 1 hour at 37° C., prior to the color developed using TMB as a substrate. The reaction was stopped by 2 N sulfuric acid at 5 min, and the absorbance was measured at 450 nm.

Figure 4:
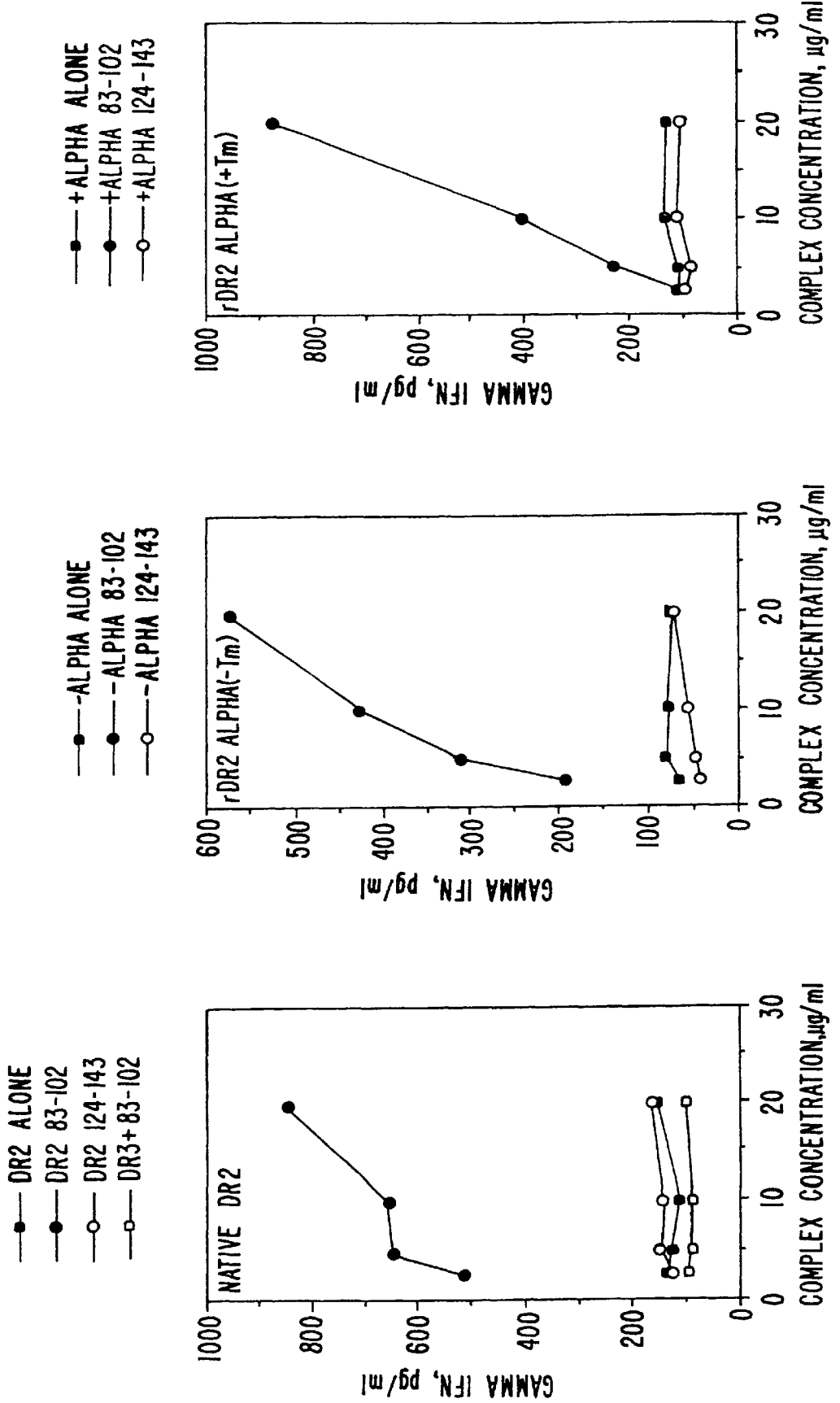
FIG. 4 shows γIFN production in T cells contacted with complexes of the invention.
Figure 5:
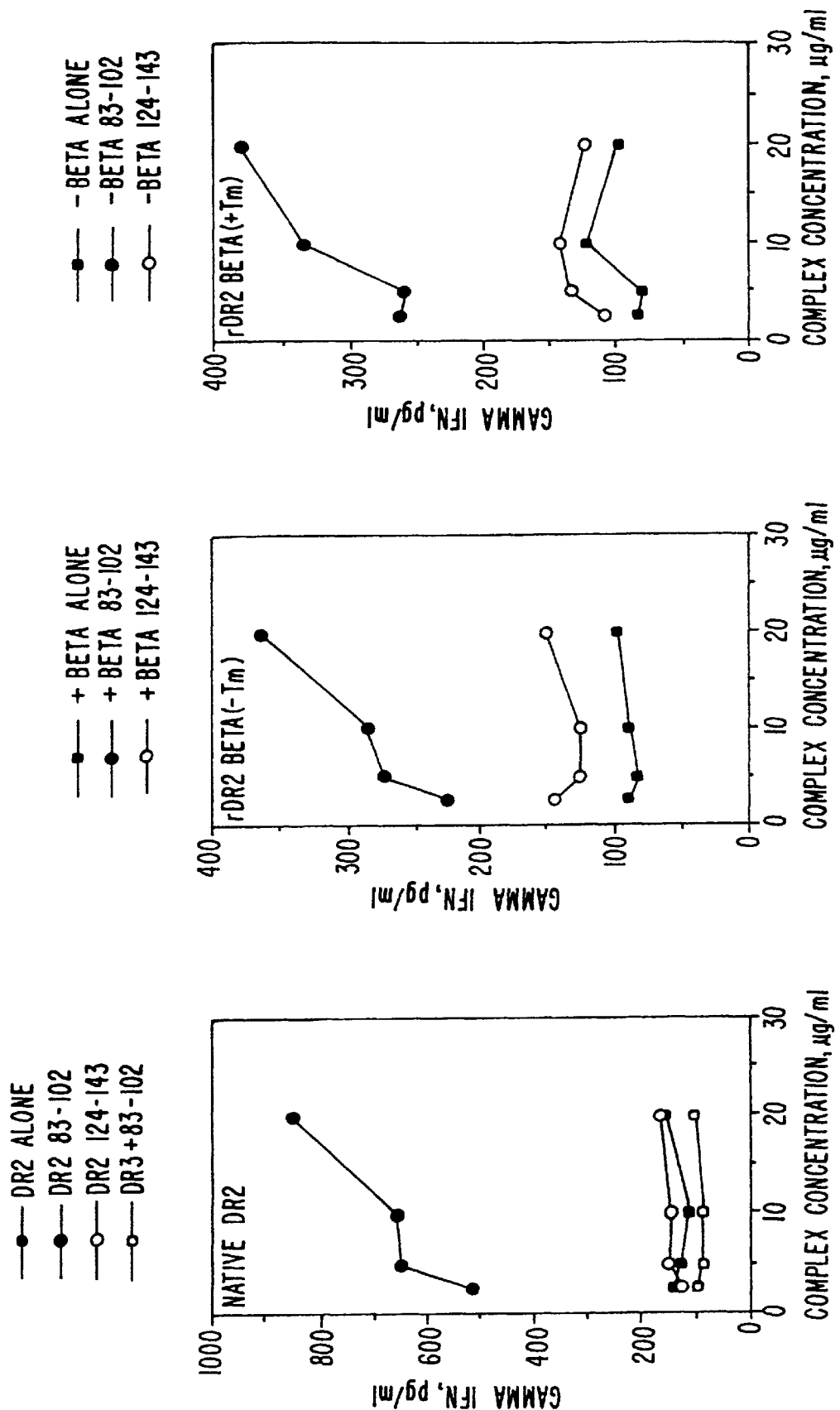
FIG. 5 shows γIFN production in T cells contacted with complexes of the invention.

The increase in gamma IFN production of T cells has been shown to occur following TCR occupancy by specific ligands. The complexes of native DR2 with MBP (83–102) $Y^{83}$ peptide were used as a positive control in this assay. The specificity of the increase in gamma IFN production was demonstrated by complexes of native DR2 or chains with irrelevant high affinity MBP (124–143) peptide in all experiments. Similarly, complexes of DR3 with MBP (83–102)$Y^{83}$ peptide was used to demonstrate the restriction of SS8T cloned T cells by HLA-DR2. Results obtained with complexes of alpha chain (with or without Tm) and beta chain (with or without Tm) are presented in FIG. 4 and FIG. 5.

These results clearly demonstrate that MHC class II single chain-peptide complexes function like complexes of antigenic peptide and native heterodimer.

EXAMPLE 6

Treatment of EAE Using Recombinantly Produced I-A$^s$ α chain

This example demonstrates the ability of the recombinantly produced single chain complexes of the invention to induce anergy in vivo. These experiments demonstrate prevention of EAE in SJL/J mice. The a chains of IA$^s$ were recombinantly expressed using the methods of the invention. Briefly, PCR primers were prepared based on the gene sequence available in Genbank to isolate the gene from mouse spleen cells. The resultant gene was expressed using expression vector p27313, as described above.

Figure 6:
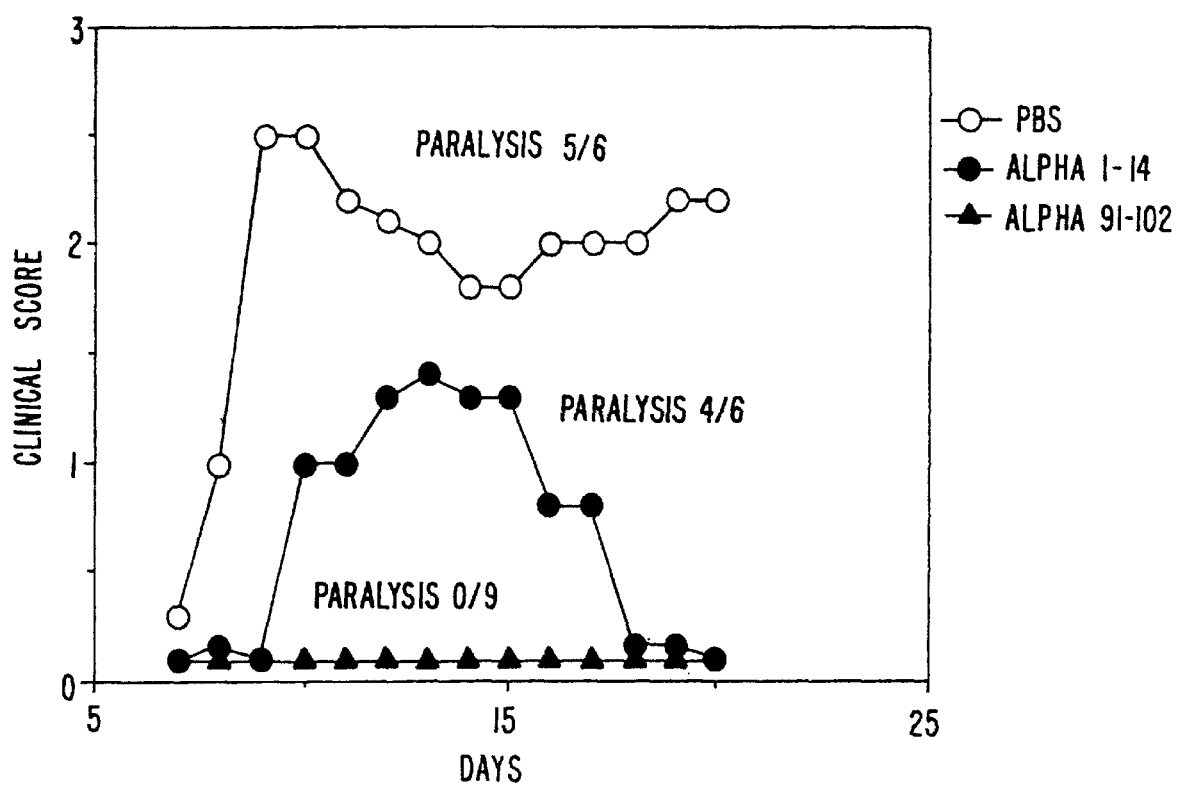
FIG. 6 shows efficacy of complexes of the invention in an animal model for multiple sclerosis.

EAE was induced by adoptive transfer of 1×10$^7$ MBP (91–103) reactive T cells as described in Sharma et al *Proc. Natl. Acad. Sci. USA* 88:11465–11469(1991). The experiment was performed using a chain of IA$^s$ complexed with MBP 91–103 or 1–14 prepared as described above. On days 0, 2, 4, and 6, each mouse received 40 µg of complexes in as described in Sharma et al. The results are shown in FIG. 6. As can be seen there, animals receiving PBS alone or irrelevant complex (I-A$^s$ complexed with MBP(1–14)) showed paralysis, whereas animals receiving relevant complex (I-A$^s$ complexed with MBP(91–103)) did not.

EXAMPLE 7

Ubiquitin Fusion Expression System for Expression of MHC in *E. coli*

Use of yeast genes encoding ubiquitin in the production of fusion proteins in *E. coli* are described in Miller et al. *Biotechnology* 7:698–704 (1989). In this system, the gene of interest is produced as a C-terminal fusion to the first 76 residues of the yeast ubiquitin gene containing the UPP cleavage site. Cleavage at the junction of the two moieties results in production of a protein having an intact authentic N-terminal reside.

Examples of such cleavage sites are the ubiquitin sequences recognized by the yeast ubiquitin protein peptidase (UPP) and ubiquitin specific protease (UBPI). UPP is the product of the YUH1 gene and can be expressed in active form in *E. coli* and used in vitro or in vivo to cleave ubiquitin-protein fusions at the fusion junction (Miller et al, supra) The efficiency of cleavage by UPP has been shown to be affected by the length of the fusion product and cleavage of fusions greater than 20 Kd are often inefficient. However, UBP1 has been shown by Tobias and Varshavsky *J. Biol. Chem.* 266:12021 (1991) to have the same proteolytic properties of UPP but not affected by the size of the fusion.

Taking into account that the predicted size of a ubiquitin-DR2 alpha fusion is $M_r$30738, and the finding that cleavage by UPP is inefficient with proteins of this size, UBP1 would be preferred for this system.

Two approaches can be taken to make use of the ubiquitin system for production of "authentic" MHC II chains in *E. coli*. First, either UPP or UBP1 could be cloned and expressed in *E. coli* and cell extracts from induced cells used in vitro to cleave the fusion protein (which would be made separately). Secondly, either UPP or UBP1 could be supplied in vivo for simultaneous expression with the MHC II chain resulting in the production of "authentic" MHC II directly from the crude cell extract.

Construction of Ubiquitin Fusion Vector p27340. The sequence encoding the 76 amino-acid coding region of ubiquitin was amplified from yeast genomic DNA by PCR. The primers were designed based on the Ubi76 sequence in Genbank. The primers were as follows:

Ubi "top" primer

```
                        BamHI
                        -------
5'...TCAGGATCCGATCGTGGAGGATGATTAAATGCAAATTTTTGTCAAGACTTTGACTGGT...3'   (SEQ. ID. No. 16)
```

The primer sequence includes the phi-10 coupler region and the underlined sequence represents the actual ubiquitin 5' sequence. Ubi "reverse" primer

```
        EcoRI     SacII
        -------   -----
5'...TGAATTCCCGCGGAGTCTCAAGACTAAGTGCAAAGTGGA...3'  (SEQ. ID. No. 17)
```

The unique SacII site is generated by altering the base sequence so as to create the restriction site for fusion cloning but maintaining the amino acid sequence of the molecule.

An expression vector for production of desired fusion products, p27340, was generated by digesting p27313, described above, with BamHI and EcoRI and ligating the 5500 bp fragment with the 259 bp ubi-76 PCR product digested with the same enzymes.

p27340 which can be used to fuse any gene to the ubiquitin gene so as to make a fusion product which can then be specifically cleaved to yield a protein of desired N-terminus. The vector is selectable with ampicillin.

The nucleic acid encoding the DR alpha chain lacking its transmembrane region was cloned in p27340 and was expressed as a fusion product of expected molecular weight of 30,758 daltons. SDS-PAGE gels showed the presence of a double band similar to the expression products from plasmid p26495.

Construction of p27351 and 27373. The DR alpha chain sequences were amplified using PCR to generate the full length sequence as well as the sequence lacking the transmembrane and cytoplasmic domains. The PCR primers designed for the fusion of these sequences to the ubiquitin 76 sequence were as follows:

Alpha-ubi76 Primer(top strand)

p27351 was generated by digesting p27340 with SacII and EcoRI and ligating the 5740 bp fragment with the 589 bp fragment of the DR ΔTM alpha PCR product digested with the same enzymes. The plasmid p27373 expresses DR alpha lacking the transmembrane domain and ten more residues from the extracellular domain fused to Ubiquitin 76 sequence.

Construction of p32941. The DR alpha full-length sequence was obtained by PCR amplification of p27317. The PCR primers were designed so as to contain the restriction enzyme sites SacII and EcoRI and these were used to subclone the PCR-amplified fragment into p27340.

The plasmid was transformed into the expression host W3110/DE3. Following growth and IPTG induction, expression of the fusion protein of Ubiquitin 76+DR alpha F/L of the expected molecular weight $M_r$=34,625 was observed.

EXAMPLE 8

Additional *E. coli* MHC II Expression Plasmids

Construction of p28524 for Expression of DR alpha ΔTM Chain that is Shorter by 10 Residues. The plasmid p26495 expresses DR alpha ΔTM chain in the pET expression system. Upon IPTG inductions, the SDS-PAGE gel shows a doublet of bands at the expected molecular weight. These

```
         SacII
         -------
5'...ATCCGCGGGGCATCAAAGAAGAACATGTGATCATC...3'   (SEQ. ID. No. 18)
```

The sequence comprising the SacII site regenerates the ubiquitin cleavage site when fused to the ubi-76 gene. The underlined sequence represents the DR alpha chain without its initial methionine codon.

Alpha F/L Primer(bottom strand)

bands were sequenced for the first 5 N-terminal residues and both gave the correct sequence for the alpha chain. Plasmid p28524 was constructed to generate a even more truncated version of DR alpha ΔTM chain. The sequence was PCR amplified using the following primers:

```
         EcoRI
         -------
5'...GTCGAATTCTTACAGAGGCCCCCTGCGTT...3'   (SEQ. ID. No. 19)
```

Alpha ΔTM Primer(bottom strand)

```
         EcoRI
         -------
5'...GTCGAATTCTCAGTTCTCTGTAGTCTCTGGGAG...3'   (SEQ. ID. No. 20)
```

Alpha ΔTM-10 Primer(bottom strand)

```
5'...ATCGAATTCTTAAGCATCAAACTCCCAGTGCTT...3'   (SEQ. ID. No. 21)
```

Top strand primer:
5'...CGGGATCCGATCGTGGAGGATGATTAAATGATCAAAGAAGAACATGTGATCAT...3'  (SEQ. ID. No. 22)

Bottom strand primer:
5'...ATCGAATTCTTAAGCATCAAACTCCCAGTGCTT...3'  (SEQ. ID. No. 23)

The PCR product was digested with BamHI and EcoRI and cloned into p27313 digested with the same enzymes.

Construction of E. coli Expression Plasmid with Tetracycline Resistance. The following plasmids were constructed for expression of MHC class II single chains in E. coli. Plasmids p26495, p26496, p27316 and p27317 described above express ΔTM and full-length DR alpha and beta chains in the presence of ampicillin resistance. For scale-up culturing of E. coli strains, ampicillin is not an effective antibiotic as it is degraded rapidly due to the β-lactamase secreted by the cells containing amp resistant plasmids. Therefore tetracycline resistance gene was cloned into the above plasmids to make them more stable under fermentation conditions.

Construction of p27329 and p27330. The tetracycline resistance gene was amplified by PCR using pBR322 as target DNA and the following PCR primers:

Top strand primer:
5'...AT<u>CTCGAG</u>TTTGACAGCTTATCATCG...3'  (SEQ. ID. No. 24)
      Ava 1

Bottom strand primer:
5'...AT<u>CTCGAG</u>TCAGGTCGAGGTGGC...3'  (SEQ. ID. No. 25)
      Ava 1 p27329 was generated by linearizing p27316 with AvaI and phosphatasing the 6245 bp fragment with calf intestinal phasphatase. This fragment was ligated to the Tetracycline PCR product digested with AvaI. The resulting plasmid expresses DRB5*0101 full-length chain in the presence of both ampicillin and tetracycline markers.

p27330 was generated by similar manipulations starting with AvaI digested p27317 and cloning in the Tetracycline PCR product. The resulting plasmid expresses DR alpha full-length chain in the presence of both ampicillin and tetracycline markers.

Construction of p329129 and p33435. The tetracycline gene was cloned into p28524 and p26496 by restriction digestion. Plasmids p26495 or p26496 were digested with XbaI and AvaI. The resulting 3736 bp fragment was ligated to the 3507 bp fragment generated by digestion of p27329 with XbaI+AvaI+PstI. The resulting plasmids express DR alpha and beta ΔTM chains in the presence of ampicillin and tetracycline markers.

EXAMPLE 9

Fermentation of E. coli Strains Expressing MHC Class II Single Chains

A ten-liter microferm system was purchased from New Brunswick Scientific. The system included features which allow for monitoring and control over pH, $dO_2$, temperature, and agitation rate. In addition, the system was supplied with a pump for use in continuous feed of media to the fermentation broth.

All the MHC class II single chains expressed in the E. coli host W3110/DE3 were expressed under typical fermentation conditions to obtain high yields of proteins. Induction was carried out at an $OD_{600}$ of approximately 20. The cells were harvested 2 hours following induction and processed for inclusion body preparation. A typical fermentation run generates wet cell pastes on the scale of 500 g which can be frozen at −20° C. and processed for lysis in batches.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

---

What is claimed is:

1. A method of producing a functional MHC class II polypeptide comprising an antigen binding site and sequences necessary for recognition by the appropriate T cell receptor and capable of binding an antigenic pettide and being recognized by an appropriate T cell, the method comprising;
    a) growing in culture a prokaryotic cell containing an expression vector comprising a nucleotide sequence encoding the MHC class II polypeptide under conditions such that the polypeptide is expressed; and
    b) isolating the functional MHC polypeptide without complex refolding steps.

2. A method of claim 1, wherein the cell comprises nucleotide sequences encoding two MHC polypeptites.

3. A prokaryotic expression vector comprising a nucleotide sequence encoding a functional MHC class II polypeptide capable of binding an antigenic peptide and being recognized by an appropriate T cell receptor, said polypeptide comprising an antigen binding site and sequences necessary for recognition by the appropriate T cell receptor, operably linked to a prokaryotic promoter sequence.

4. A vector of claim 3, wherein the nucleotide sequence encoding the MHC polypeptide is operably linked to a nucleotide sequence encoding a signal sequence.

5. A vector of claim 3, wherein the nucleotide sequence codes for a truncated MHC polypeptide.

6. A vector of claim 5, wherein the MHC polypeptide lacks a transmembrane domain.

7. A prokaryotic cell comprising the vector of claim 3.

8. A cell of claim 7, wherein the cell is *E. coli*.

* * * * *